US012653678B2

(12) United States Patent
Christopher et al.

(10) Patent No.: US 12,653,678 B2
(45) Date of Patent: Jun. 16, 2026

(54) UNIVERSAL LOW-PROFILE INTERCRANIAL ASSEMBLY

(71) Applicant: LONGEVITI NEURO SOLUTIONS, INC., Baltimore, MD (US)

(72) Inventors: Jesse Christopher, Hunt Valley, MD (US); Chad R. Gordon, Cockeysville, MD (US); Bradley Rabinovitz, Severna Park, MD (US)

(73) Assignee: LONGEVITI NEURO SOLUTIONS, INC., Baltimore, MD (US)

( * ) Notice: Subject to any disclaimer, the term of this patent is extended or adjusted under 35 U.S.C. 154(b) by 687 days.

(21) Appl. No.: 18/158,677

(22) Filed: Jan. 24, 2023

(65) Prior Publication Data

US 2023/0157826 A1 May 25, 2023

Related U.S. Application Data

(63) Continuation of application No. 16/203,357, filed on Nov. 28, 2018, now Pat. No. 11,589,992.

(60) Provisional application No. 62/615,209, filed on Jan. 9, 2018.

(51) Int. Cl.
*A61F 2/28* (2006.01)
*A61F 2/30* (2006.01)
*A61N 1/375* (2006.01)

(52) U.S. Cl.
CPC ........ *A61F 2/2875* (2013.01); *A61F 2/30942* (2013.01); *A61N 1/37518* (2017.08); *A61F 2002/2835* (2013.01); *A61F 2002/3096* (2013.01); *A61F 2310/00023* (2013.01)

(58) Field of Classification Search
CPC ................ A61F 2/2875; A61F 2/30942; A61F 2002/2835; A61N 1/0541; A61N 1/0529; A61B 2090/103
See application file for complete search history.

(56) References Cited

U.S. PATENT DOCUMENTS

| | | | |
|---|---|---|---|
| 4,206,762 A | 6/1980 | Cosman | |
| 4,265,252 A | 5/1981 | Chubbuck et al. | |
| 4,281,666 A | 8/1981 | Cosman | |
| 4,436,684 A | 3/1984 | White | |
| 4,660,568 A | 4/1987 | Cosman | |
| 4,805,634 A | 2/1989 | Ullrich et al. | |

(Continued)

FOREIGN PATENT DOCUMENTS

| | | |
|---|---|---|
| CN | 103598883 A | 2/2014 |
| JP | 2000339465 A | 12/2000 |

(Continued)

OTHER PUBLICATIONS

Sing, Mansher et al, "Countersinking" of reservoir in an irradiated patients can decrease tension on scalp closure, Surgical Neurology International, 2015; 6(Suppl 11): SS34-S.

(Continued)

*Primary Examiner* — Alvin J Stewart
(74) *Attorney, Agent, or Firm* — Welsh Flaxman & Gitler LLC

(57) ABSTRACT

A universal low-profile intercranial assembly includes a mounting plate and a low profile intercranial device composed of a static cranial implant and an interdigitating functional neurosurgical implant. The low profile intercranial device is shaped and dimensioned for mounted to the mounting plate.

8 Claims, 14 Drawing Sheets

(56) References Cited

U.S. PATENT DOCUMENTS

| | | |
|---|---|---|
| 5,218,975 A | 6/1993 | Prostkoff |
| 5,503,164 A | 4/1996 | Friedman |
| 5,545,226 A | 8/1996 | Wingo et al. |
| 5,741,215 A | 4/1998 | D'Urso |
| 5,824,332 A | 10/1998 | Jannetta |
| 6,006,124 A | 12/1999 | Fischell et al. |
| 6,016,449 A | 1/2000 | Fischell et al. |
| 6,061,593 A | 5/2000 | Fischell et al. |
| 6,248,126 B1 | 6/2001 | Lesser et al. |
| 6,354,299 B1 | 3/2002 | Fischell et al. |
| 6,366,813 B1 | 4/2002 | DiLorenzo |
| 6,427,086 B1 | 7/2002 | Fischell et al. |
| 6,485,464 B1 | 11/2002 | Christensen et al. |
| 6,560,486 B1 | 5/2003 | Osorio et al. |
| 6,618,623 B1 | 9/2003 | Pless et al. |
| 6,726,678 B1 | 4/2004 | Nelson et al. |
| 6,819,956 B2 | 11/2004 | DiLorenzo |
| 6,882,881 B1 | 4/2005 | Lesser et al. |
| 6,931,284 B2 | 8/2005 | Engmark et al. |
| 6,932,842 B1 | 8/2005 | Litschko et al. |
| 7,050,877 B2 | 5/2006 | Iseki et al. |
| 7,113,841 B2 | 9/2006 | Abe et al. |
| 7,158,833 B2 | 1/2007 | Pless et al. |
| 7,209,787 B2 | 4/2007 | DiLorenzo |
| 7,212,864 B2 | 5/2007 | Wahlstrand et al. |
| 7,231,254 B2 | 6/2007 | DiLorenzo |
| 7,242,982 B2 | 7/2007 | Singhal et al. |
| 7,242,984 B2 | 7/2007 | DiLorenzo |
| 7,263,401 B2 | 8/2007 | Scott et al. |
| 7,277,758 B2 | 10/2007 | DiLorenzo |
| 7,324,851 B1 | 1/2008 | DiLorenzo |
| 7,346,391 B1 | 3/2008 | Osorio et al. |
| 7,392,089 B2 | 6/2008 | Wahlstrand et al. |
| 7,529,586 B2 | 5/2009 | Wahlstrand et al. |
| 7,565,199 B2 | 7/2009 | Sheffield et al. |
| 7,596,399 B2 | 9/2009 | Singhal et al. |
| 7,596,408 B2 | 9/2009 | Singhal et al. |
| 7,647,097 B2 | 1/2010 | Flaherty et al. |
| 7,657,316 B2 | 2/2010 | Jaax et al. |
| 7,684,866 B2 | 3/2010 | Fowler et al. |
| 7,747,305 B2 | 6/2010 | Dean et al. |
| 7,747,318 B2 | 6/2010 | John et al. |
| 7,848,817 B2 | 12/2010 | Janzig et al. |
| 7,887,501 B2 | 2/2011 | Riordan et al. |
| 7,894,905 B2 | 2/2011 | Pless et al. |
| 7,918,887 B2 | 4/2011 | Roche |
| 7,935,858 B2 | 5/2011 | Praetzel |
| 8,086,336 B2 | 12/2011 | Christensen |
| 8,116,875 B2 | 2/2012 | Osypka et al. |
| 8,182,540 B2 | 5/2012 | Lin et al. |
| 8,202,090 B2 | 6/2012 | Shachar |
| 8,235,903 B2 | 8/2012 | Abraham |
| 8,306,607 B1 | 11/2012 | Levi et al. |
| 8,397,732 B2 | 3/2013 | Singhal et al. |
| 8,454,701 B2 | 6/2013 | Devauchelle et al. |
| 8,457,744 B2 | 6/2013 | Janzig et al. |
| 8,591,562 B2 | 11/2013 | D'Ambrosio et al. |
| 8,706,285 B2 | 4/2014 | Narainasamy et al. |
| 8,761,889 B2 | 6/2014 | Wingeier et al. |
| 8,781,557 B2 | 7/2014 | Dean et al. |
| 8,938,290 B2 | 1/2015 | Wingeier et al. |
| D723,162 S | 2/2015 | Brogan et al. |
| 8,956,418 B2 | 2/2015 | Wasielewski et al. |
| 8,965,513 B2 | 2/2015 | Wingeier et al. |
| 8,974,535 B2 | 3/2015 | Antonyshyn et al. |
| 9,014,810 B2 | 4/2015 | Sauter-Starace et al. |
| 9,044,195 B2 | 6/2015 | Manwaring et al. |
| 9,078,755 B2 | 7/2015 | Mahfouz |
| 9,084,901 B2 | 7/2015 | Wahlstrand |
| 9,101,341 B2 | 8/2015 | Fitzgerald et al. |
| 9,149,564 B2 | 10/2015 | Jin et al. |
| 9,162,072 B2 | 10/2015 | Singhal et al. |
| 9,167,976 B2 | 10/2015 | Wingeier et al. |
| 9,167,977 B2 | 10/2015 | Wingeier et al. |
| 9,167,978 B2 | 10/2015 | Wingeier et al. |
| 9,179,850 B2 | 11/2015 | Wingeier et al. |
| 9,216,084 B2 | 12/2015 | Gordon et al. |
| 9,289,143 B2 | 3/2016 | Wingeier et al. |
| 9,375,564 B2 | 6/2016 | Wingeier et al. |
| 9,387,320 B2 | 7/2016 | Wingeier et al. |
| 9,393,432 B2 | 7/2016 | Wahlstrand et al. |
| 9,421,363 B2 | 8/2016 | Krahl et al. |
| 9,421,371 B2 | 8/2016 | Pless et al. |
| 9,440,064 B2 | 9/2016 | Wingeier et al. |
| 9,462,958 B2 | 10/2016 | Osorio et al. |
| 9,474,611 B2 | 10/2016 | Restrepo et al. |
| 9,522,081 B2 | 12/2016 | D'Ambrosio et al. |
| 9,573,322 B2 | 2/2017 | Wasielewski |
| 9,592,124 B2 | 3/2017 | Joganic |
| 9,592,377 B2 | 3/2017 | Greenberg et al. |
| 9,764,510 B2 | 9/2017 | Antonyshyn et al. |
| 9,993,337 B1 * | 6/2018 | Brogan ................. A61F 2/2875 |
| 10,588,710 B2 | 3/2020 | Van Venrooji et al. |
| 11,154,401 B2 | 10/2021 | Antonyshyn et al. |
| 12,029,652 B2 * | 7/2024 | Carpentier ........... A61B 8/4281 |
| 12,048,585 B2 * | 7/2024 | Bouchoux .............. A61F 2/2875 |
| 12,383,402 B2 * | 8/2025 | Clawson ................. A61B 6/501 |
| 2002/0002390 A1 | 1/2002 | Fischell et al. |
| 2002/0140137 A1 * | 10/2002 | Sapieszko ............... C04B 32/00 |
| | | 264/629 |
| 2002/0169485 A1 | 11/2002 | Pless et al. |
| 2003/0125786 A1 | 7/2003 | Gliner et al. |
| 2004/0172090 A1 | 9/2004 | Janzig et al. |
| 2004/0176816 A1 | 9/2004 | Singhal et al. |
| 2004/0176818 A1 | 9/2004 | Wahlstrand et al. |
| 2004/0267234 A1 | 12/2004 | Heart et al. |
| 2005/0003268 A1 | 1/2005 | Scott et al. |
| 2005/0004620 A1 | 1/2005 | Singhal et al. |
| 2005/0004637 A1 | 1/2005 | Singhal et al. |
| 2005/0043835 A1 | 2/2005 | Christensen |
| 2005/0203366 A1 | 9/2005 | Donoghue et al. |
| 2005/0245984 A1 | 11/2005 | Singhal et al. |
| 2006/0194170 A1 | 8/2006 | Wohrle et al. |
| 2006/0224242 A1 | 10/2006 | Swords et al. |
| 2006/0287654 A1 | 12/2006 | Posnick |
| 2007/0038100 A1 | 2/2007 | Nita |
| 2007/0179558 A1 | 8/2007 | Gliner et al. |
| 2007/0225773 A1 | 9/2007 | Shen et al. |
| 2008/0147076 A1 | 6/2008 | Geisert et al. |
| 2009/0112278 A1 | 4/2009 | Wingeier et al. |
| 2009/0281623 A1 | 11/2009 | Kast et al. |
| 2010/0145162 A1 | 6/2010 | Devauchelle et al. |
| 2010/0292963 A1 | 11/2010 | Schroeder |
| 2011/0066072 A1 | 3/2011 | Kawoos et al. |
| 2011/0213382 A1 | 9/2011 | Decre et al. |
| 2012/0010711 A1 | 1/2012 | Antonyshyn et al. |
| 2012/0063655 A1 | 3/2012 | Dean et al. |
| 2012/0259428 A1 * | 10/2012 | Brogan ................. A61F 2/0059 |
| | | 623/23.72 |
| 2013/0066431 A1 * | 3/2013 | Funderburk .......... A61F 2/2875 |
| | | 623/17.19 |
| 2013/0247644 A1 | 9/2013 | Swoboda et al. |
| 2013/0282011 A1 | 10/2013 | Brogan et al. |
| 2013/0304217 A1 * | 11/2013 | Recber .................. A61F 2/2875 |
| | | 30/115 |
| 2013/0345599 A1 | 12/2013 | Lin et al. |
| 2014/0249454 A1 | 9/2014 | Carpentier |
| 2014/0309744 A1 | 10/2014 | Batty et al. |
| 2014/0343350 A1 | 11/2014 | Martinson et al. |
| 2014/0350635 A1 | 11/2014 | Strother et al. |
| 2014/0378783 A1 | 12/2014 | Ledet et al. |
| 2015/0051455 A1 | 2/2015 | Wasielewski et al. |
| 2015/0105858 A1 | 4/2015 | Papay et al. |
| 2015/0157862 A1 | 6/2015 | Greenberg et al. |
| 2015/0231594 A1 | 8/2015 | Aguilar-Mendoza et al. |
| 2015/0289980 A1 | 10/2015 | Hirata et al. |
| 2015/0328004 A1 | 11/2015 | Mafhouz |
| 2015/0351915 A1 | 12/2015 | DeFelice et al. |
| 2016/0007874 A1 | 1/2016 | Ma et al. |
| 2016/0045723 A1 | 2/2016 | Bornzin et al. |
| 2016/0083573 A1 | 3/2016 | Berdin et al. |
| 2016/0184100 A1 * | 6/2016 | Joganic .................... A61F 2/50 |
| | | 623/17.19 |
| 2016/0185046 A1 | 6/2016 | Littlefield |

(56) References Cited

U.S. PATENT DOCUMENTS

| | | | |
|---|---|---|---|
| 2016/0193048 A1 | 7/2016 | Prada | |
| 2016/0263277 A1 | 9/2016 | Kim et al. | |
| 2016/0296312 A1 | 10/2016 | Kohn et al. | |
| 2016/0346091 A1 | 12/2016 | Bin Abdul Rahman et al. | |
| 2017/0049351 A1 | 2/2017 | Esteller | |
| 2017/0049398 A1 | 2/2017 | Hirata et al. | |
| 2017/0156596 A1 | 6/2017 | Aguilar-Mendoza et al. | |
| 2017/0368330 A1 | 12/2017 | Silay et al. | |
| 2018/0021137 A1* | 1/2018 | Sandoval | A61N 1/0539 623/17.19 |
| 2018/0055640 A1* | 3/2018 | Gordon | B33Y 50/00 |
| 2018/0185674 A1 | 7/2018 | Bauer et al. | |
| 2018/0325672 A1* | 11/2018 | Gordon | A61B 17/8085 |
| 2019/0060637 A1* | 2/2019 | Duijsens | A61N 1/0539 |
| 2020/0030099 A1* | 1/2020 | Sampath | A61B 8/4416 |
| 2020/0030103 A1* | 1/2020 | Di Meco | G05B 19/4097 |
| 2020/0197180 A1* | 6/2020 | Christopher | A61B 5/0059 |
| 2020/0390944 A1* | 12/2020 | Williams | A61B 17/064 |
| 2020/0391022 A1* | 12/2020 | Rabinovitz | A61N 1/37514 |
| 2021/0260280 A1* | 8/2021 | Gordon | A61M 39/0247 |
| 2022/0110607 A1* | 4/2022 | Bouchoux | A61F 2/2875 |
| 2022/0183844 A1* | 6/2022 | Clawson | A61B 8/4209 |
| 2022/0249190 A1* | 8/2022 | Kelly | A61B 17/3417 |
| 2022/0296375 A1* | 9/2022 | Gordon | A61B 8/4209 |
| 2023/0010415 A1* | 1/2023 | Christopher | A61B 5/031 |
| 2023/0020551 A1* | 1/2023 | Christopher | A61F 2/2875 |
| 2023/0075205 A1* | 3/2023 | Moran | A61N 1/0531 |

FOREIGN PATENT DOCUMENTS

| | | | |
|---|---|---|---|
| JP | 2008194426 | | 8/2008 |
| KR | 1020120088928 | | 8/2012 |
| WO | 2012063377 | A1 | 5/2012 |
| WO | 2012147114 | A1 | 11/2012 |
| WO | 2015081025 | A1 | 6/2015 |
| WO | 2015081027 | A1 | 6/2015 |
| WO | 2015081140 | A1 | 6/2015 |
| WO | 2015081177 | A1 | 6/2015 |
| WO | 2015081225 | A1 | 6/2015 |
| WO | 2015081232 | A1 | 6/2015 |
| WO | 2015081247 | A1 | 6/2015 |
| WO | 2015157554 | A1 | 10/2015 |
| WO | 2016086049 | A1 | 6/2016 |
| WO | 2016086054 | A1 | 6/2016 |
| WO | 2017039762 | A1 | 3/2017 |
| WO | 2017046300 | A1 | 3/2017 |
| WO | 2018064239 | A1 | 4/2018 |
| WO | 2012047759 | A1 | 4/2021 |

OTHER PUBLICATIONS

Wei et al., Implant Site Infection and Bone Flap Osteomyelitis Associated with NeuroPace Responsive Neurotimulation System. World Neurosurg. Apr. 2016;88:687.e1-6.

Majstorovic, M. "Critical Analysis on the Anatomics Acrylic Custom Cranial Implant" A Collection of Digital Media & Social Communications, May 1, 2017, pp. 1-9, https://miamajs.wordpress.com/2017/05/01/critical-analysis-on-the-anatomics-acrylic-custom-cranial-implant/.

Aatman M. Shah, Henry Jung, and Stephen Skirboll, Materials used in cranioplasty: a history and analysis, Apr. 2014, pp. 1-7, Neurosurg Focus, vol. 26. DOI: 10.3171/2014.2.FOCUS13561.

A.E. Abdulai, M.I. Iddrissu and T.K. Dakurah, Cranioplasty Using Polymethyl Methacrylate Implant Constructed from an Alginate Impression and Wax Elimination Technique, Mar. 2006, pp. 18-21, vol. 40, No. 1, Ghana Medical Journal.

L.C. Hieu, E. Bohez, J. Vander Sloten, P. Oris, H.N. Phien, E. Vatcharaporn and P.H. Binh, Design and manufacturing of Cranioplasty Implants by 3-axis CNC Milling, Feb. 20, 2002, pp. 1-11, Technology and Health Care, IOS Press.

J. Tobias, K. Hynynen, R. Roemer, A.N. Guthkelch, A.S. Fleischer, J. Shively, An ultrasound window to perform scanned, focused ultrasound hyperthermia treatments of brain tumors, Mar./Apr. 1987, pp. 228-234, Medical Physics, vol. 14, No. 2.

Ledesma et al., Responsive Neurostimulation System (RNS) in selling of cranioplasty and history of multiple craniotomies, Interdisciplinary Neurosurgery, vol. 5, Sep. 2016, pp. 29-31.

* cited by examiner

100

100

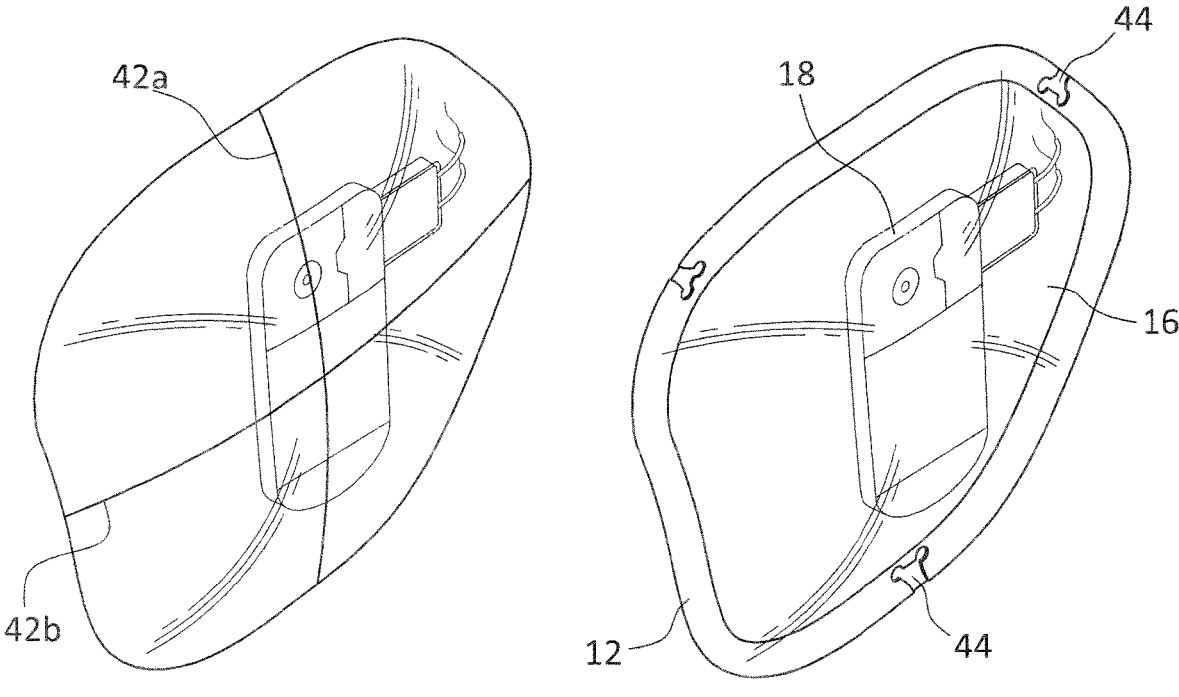
FIG. 14          FIG. 15
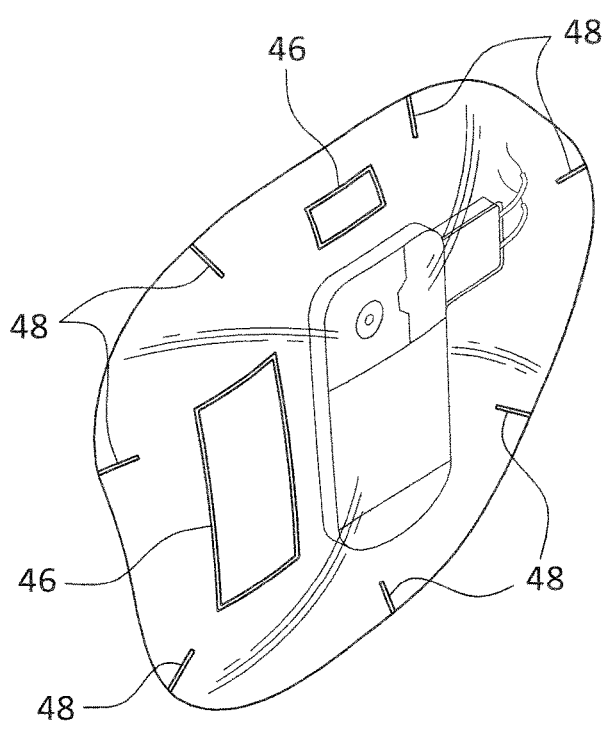
FIG. 16

UNIVERSAL LOW-PROFILE INTERCRANIAL ASSEMBLY

CROSS REFERENCE TO RELATED APPLICATION

This application is a continuation of U.S. patent application Ser. No. 16/203,357, entitled "UNIVERSAL LOW-PROFILE INTERCRANIAL ASSEMBLY," filed Nov. 28, 2018, which claims the benefit of U.S. Provisional Patent Application Ser. No. 62/615,209, entitled "UNIVERSAL LOW-PROFILE INTERCRANIAL ASSEMBLY," filed Jan. 9, 2018, both of which are incorporated herein by reference.

BACKGROUND OF THE INVENTION

1. Field of the Invention

The present invention relates to neurosurgery, plastic surgery, craniofacial surgery, and intercranial devices. More particularly, the present invention relates to a universal low-profile intercranial device allowing for ready modification and replacement of functional components thereof for the purpose of functional neurosurgery.

2. Description of the Related Art

During cranioplasty procedures, diseased or damaged portions of the skull are safely removed and replaced, while the brain is exposed underneath without injury. However, a similar operation could also be done in areas of normal, healthy cranial bone—in instances where a neuromodulation device is needed for implantation but the contour and appearance is challenging (and normal skull bone would therefore be removed and left off permanently in exchange for "housing" the neuromodulation device with a cranial implant), such as in non-bearing scalp areas such as frontal or temporal regions. Similarly, following resection of diseased cranial bone (or normal bone in cosmetically-sensitive areas), such craniectomy defects are often reconstructed with custom craniofacial implants (CCIs)—as opposed to using generic, "off-the-shelf" materials.

Historically, however, cranioplasty patients were limited to receiving custom craniofacial implant-based reconstruction—for an ideal appearance and outcome—only to "second-stage" operations, in instances where pre-existing skull defects existed—so that the exact fit and design could be obtained via CT scan and implant design could be perfected accordingly. However, recent modifications to this approach by Gordon et al. (See, Berli J, et al., "Single-stage cranioplasty reconstruction with implants." J Craniofac Surg 2016) have popularized the option of "single-stage cranioplasties"—by which a reconstructive surgeon, manually reshapes/resizes a previously-ordered, custom implant (with oversized dimensions) to fit perfectly into the skull defect— as opposed to using "off-the shelf" materials. Either way, for single-stage methods involving skull tumors or second-stage cranioplasties for pre-defined skull defects, the advent of computer-aided design/manufacturing (CAD/CAM), has provided surgeons with perfectly-shaped custom craniofacial implants designed and manufactured based in part on fine cut preoperative computed tomography (CT) scans and three-dimensional reconstruction (with or without stereolithographic models).

In fact, recent reports suggest that the use of custom craniofacial implants can improve cosmesis, decrease operative times, prevent scalp-related wound complications, and enhance patient satisfaction—and therefore, they serve as an ideal medium for reconstructing neurosurgery patients. Similarly, all custom craniofacial implants up until now have been used to replace abnormal bone having some form of disease, either of benign or malignant etiology. These customized skull implants may be termed "static custom craniofacial implants"—mainly because their main constant (i.e., unchanged purpose with respect to time) purpose encompasses strictly two benefits following placement—"brain protection" and "enhanced appearance". In addition, they may be made out of a clear acrylic (or poly methyl methacrylate) substance for enhanced sub-implant visualization, which was previously described in Applicants' own U.S. Provisional Patent Application Ser. No. 62/489,036, entitled "METHOD FOR PERFORMING SINGLE-STAGE CRANIOPLASTY RECONSTRUCTION WITH A CLEAR CUSTOM CRANIAL IMPLANT," filed Apr. 24, 2017. Meanwhile, there are other "off-the-shelf" neurological implants that have functionality, such as delivering electrical impulses to interrupt seizure activity, but they are not customizable or designed ahead-of-time with ideal shape/ size to protect the brain and restore cranial symmetry. Most of these so-called functional neurological implants fall into two categories: Deep Brain Stimulators (DBS) and Cortical Brain Stimulators (CBS). Modern day neurologic devices are confronted and challenged with high extrusion and infection risk (i.e., current flaws in modern day devices lead to high incidence of extrusion through skin thereby requiring premature explanation) approaching 50%. Similarly, battery-powered, low-profile devices for intercranial placement currently do not exist on the market. As such, the field of neurosurgery has been hampered and limited in many areas including examples like battery-powered neuromodulation cortical stimulation and delivery of neurological medicines. However, the world's first in-human experience with a battery-empowered neuromodulation device, encapsulated for the first time ever within a customized cranial implant, was recently reported in Operative Neurosurgery by Gordon et al in October 2017 (See, Gordon C R, First In-Human Experience with Complete Integration of Neuromodulation Device Within a Customized Cranial Implant. Oper Neurosurg 2017).

But with increasing experience and surgical complication rates exceedingly low, the custom craniofacial implants can also be modified in real-time for scenarios where more or less skull bone is removed and the skull defect dimensions do not match up perfectly to the pre-fabricated custom craniofacial implant (versus as originally envisioned, for example, as designed in a planning stage)—which is the scenario described within the aforementioned journal article. Or in a scenario where normal bone is to be removed simply to assure proper contour with neuromodulation implantation, one could use a pre-fabricated cutting guide for custom cranial implant placement.

Due to the recent reductions for time needed to design, fabricate and implant custom craniofacial implants, more cranioplasty procedures with alloplastic implants are being performed around the world than ever before. Accordingly, these recent developments in custom craniofacial implant sterility, shape design, and streamline production—together provide an opportunity that extends custom craniofacial implant-based cranioplasty beyond only patients who require replacement of pre-existing craniectomy defects.

SUMMARY OF THE INVENTION

It is, therefore, an object of the present invention to provide a universal low-profile intercranial assembly including a mounting plate and a low profile intercranial device. The low profile intercranial device includes a static cranial implant and an interdigitating functional neurosurgical implant. The low profile intercranial device is shaped and dimensioned for mounting to the mounting plate.

It is also an object of the present invention to provide a universal low-profile intercranial assembly wherein the mounting plate include a hollowed-out center aperture shaped and dimensioned for the ready placement and mounting of the low profile intercranial device therein.

It is another object of the present invention to provide a universal low-profile intercranial assembly wherein the static cranial implant includes a hollowed-out center cavity shaped and dimensioned for optimal anatomical placement of the functional neurosurgical implant within the confines of the center cavity.

It is a further object of the present invention to provide a universal low-profile intercranial assembly wherein the static cranial implant also includes structural elements accommodating features of the functional neurosurgical implant.

It is also an object of the present invention to provide a universal low-profile intercranial assembly wherein the mounting plate includes an outer convex first surface, an inner concave second surface, and a peripheral edge extending between the first surface and the second surface, as well as a center aperture accommodating the static cranial implant.

It is another object of the present invention to provide a universal low-profile intercranial assembly wherein the mounting plate is fabricated from clear and/or opaque PMMA (Poly(methyl methacrylate)), PEEK (Polyether ether ketone), PEKK (Polyetherketoneketone), porous polyethylene, titanium alloy, allograft, autograft, xenograft, and/or other tissue-engineered constructs.

It is a further object of the present invention to provide a universal low-profile intercranial assembly wherein the mounting plate has a thickness of 1 millimeter to 25 millimeters.

It is also an object of the present invention to provide a universal low-profile intercranial assembly wherein the static cranial implant includes an outer convex first surface, an inner concave second surface, and a peripheral edge extending between the first surface and the second surface, as well as a cavity accommodating the functional neurosurgical implant.

It is another object of the present invention to provide a universal low-profile intercranial assembly wherein the static cranial implant is fabricated from clear and/or opaque PMMA (Poly(methyl methacrylate)), PEEK (Polyether ether ketone), PEKK (Polyetherketoneketone), porous polyethylene, titanium alloy, allograft, autograft, xenograft, and/or various other tissue-engineered constructs.

It is a further object of the present invention to provide a universal low-profile intercranial assembly wherein the static cranial implant has a thickness of 1 millimeter to 25 millimeters.

It is also an object of the present invention to provide a universal low-profile intercranial assembly wherein the static cranial implant has a multiple-piece construction.

It is another object of the present invention to provide a universal low-profile intercranial assembly wherein the functional neurosurgical implant is used in the treatment of epilepsy, movement disorders, chronic pain, spasticity, cerebral palsy, multiple sclerosis, spinal cord injury, traumatic brain injury, attention-deficit/hyperactivity disorder, or autism.

It is a further object of the present invention to provide an intercranial assembly having a cranial implant including includes an outer first surface, an inner second surface, and a peripheral edge extending between the outer first surface and the inner second surface. The cranial implant includes topographical markings indicating thickness of the cranial implant and allowing a surgeon to readily and accurately appreciate the thickness of the cranial implant.

It is also an object of the present invention to provide an intercranial assembly wherein the topographical markings are composed of contour lines.

It is another object of the present invention to provide an intercranial assembly wherein the contour lines are produced by connecting points of equal thickness together to create a continuous line designating a specific thickness of the cranial implant at the contour line.

It is a further object of the present invention to provide an intercranial assembly wherein the contour lines are composed of specific colors designating a specific thickness.

It is also an object of the present invention to provide a universal low-profile intercranial assembly wherein the contour lines are annotated with numbers indicating the thickness of the cranial implant.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 14 is a perspective view of a low-profile intercranial device including a customized static cranial implant with alignment lines in accordance with an alternate embodiment of the present invention.

FIG. 15 is a perspective view of a universal low-profile intercranial assembly including a mounting plate with relief recesses in accordance with an alternate embodiment of the present invention.

FIG. 16 is a perspective view of a low-profile intercranial device including a customized static cranial implant with laser cuts and laser markings in accordance with an alternate embodiment of the present invention.

DESCRIPTION OF THE PREFERRED EMBODIMENTS

Figure 1:
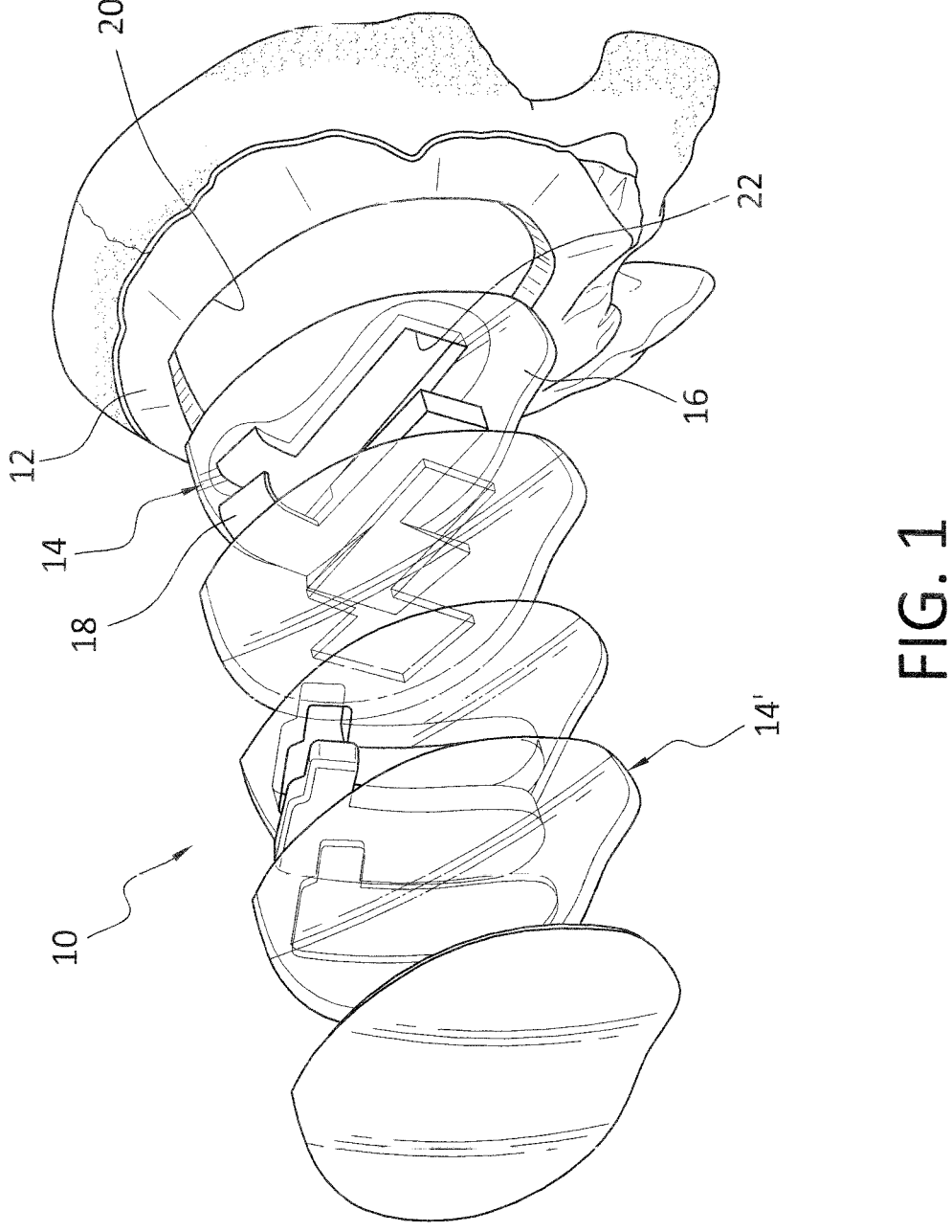
FIG. 1 is an exploded perspective view of a universal low-profile intercranial assembly with first and second low profile intercranial devices.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

As used within this disclosure, the term "intercranial" means situated or occurring within the anatomical boundaries of the cranium itself—such that such devices are positioned within the anatomical dead space existing between the inner surface of the scalp and the outer surface of the dura (i.e. outside lining of the brain). As such, intercranial devices are those devices intended for positioning within the cranium itself as opposed to devices that may be positioned on or adjacent to the cranium or positioned along the interior of the cranium, for example, between the cerebral cortex and the interior surface of the cranium. With this in mind, intercranial devices such as those discussed below replace resected portions of the cranium due to abnormalities in the cranium, damage to the cranium, or other medically sufficient reasons for resecting positions of the cranium.

With reference to the various figures, a universal low-profile intercranial assembly 10 and a method for using the universal low-profile intercranial assembly 10 are disclosed. In addition to providing the universal low-profile intercranial assembly 10 and a method for using the universal low-profile intercranial device 10, the present invention applies the manufacturing methods disclosed in commonly owned U.S. patent application Ser. No. 15/669,268, entitled "METHOD FOR MANUFACTURING A LOW-PROFILE INTERCRANIAL DEVICE AND THE LOW-PROFILE INTERCRANIAL DEVICE MANUFACTURED THEREBY," filed Aug. 4, 2017 (which has published as U.S. Patent Application Publication No. 2018/0055640), which is incorporated herein by reference. That is, the universal low-profile intercranial assembly 10 and a method for using the universal low-profile intercranial assembly 10 take advantage of virtual design and maximal interdigitating of distinct cranial implants (that is, a low-profile static cranial implant and a functional neurosurgical implant in accordance with a preferred embodiment of the present invention). The term "interdigitating" is meant to refer to the interlocking of three distinct elements (that is, the mounting plate, the static cranial implant and the functional neurosurgical implant) such that the two distinct elements mesh together to ultimately define a single product.

As mentioned above, the universal low-profile intercranial assembly 10 is generally composed of mounting plate 12 into which a low profile intercranial device 14 composed of a static cranial implant 16 and an interdigitating functional neurosurgical implant 18 are mounted in accordance with the present invention. This combination of elements results in the present universal low-profile intercranial assembly 10 that provides a mechanism whereby various low profile intercranial devices 12 may be implanted as desired and needed based upon the progress of a patient undergoing cranial and/or brain based treatments.

More specifically, the universal low-profile intercranial assembly 10 of the present invention employs a CT (Computed Tomography) scan-based, virtual design session performed pre-operatively based on the brain-specific geographical location (as opposed to the standard method of using the skull-specific geographic location). As a result, the methodology employed in accordance with the present invention accommodates both brain and skull pathology in three-dimensional space, in all three axes, prior to surgery unlike ever before.

With this information, as well as knowledge regarding the dimensions of the functional neurosurgical implant 18, the mounting plate 12 and/or the static cranial implant 16 are produced. The mounting plate 12 is augmented, reduced and/or modified to include a hollowed-out center aperture 20 shaped and dimensioned for the ready placement and mounting of the low profile intercranial device 14 therein. In this way, and as will appreciated based upon the following disclosure, the mounting plate 12 is specifically shaped and dimensioned for intercranial placement within the cranial defect while simultaneously providing a center aperture 20 into which a low profile intercranial device 14 may be readily mounted. Given that the center aperture 20 of the mounting plate 12 is of a known shape, which may be readily replicated and controlled, the shape of the low profile intercranial device 14 can be readily controlled to allow for immediate and exact placement of the low profile intercranial device 14 within the center aperture 20. This allows for a first low profile intercranial device 14 to be implanted and used at a first stage of a patient's treatment and subsequently removed and replaced with a second low profile intercranial device 14' at a second stage of the patient's treatment.

In addition to the mounting plate 12, the static cranial implant 16 is similarly augmented, reduced and/or modified to include a hollowed-out center cavity 22 (it is appreciated multiple cavities may be employed where the functional neurosurgical implant(s) 18 being used dictates that the cavity 22 need not be directly in the center of the static cranial implant 16 but may be offset as dictated by the procedure being performed), as well as other structural elements 24 (for example, wire tunnel(s), pocket(s), etc.), shaped and dimensioned for optimal anatomical placement of the functional neurosurgical implant 18 that is ultimately positioned within the confines of the center cavity 22 (and other structural elements) of the static cranial implant 16 (i.e., like an empty shell case but with exact negative and positive enhancements to optimize anatomical positioning of both the static cranial implant and the functional neurosurgical implant). Depending upon the specifics of the functional neurosurgical implant 18 positioned within the center cavity 22 of the of static cranial implant 16, various mechanical coupling mechanisms, for example, screws, plates, etc. (not shown), are used to ensure that the functional neurosurgical implant 18 is securely held in place.

As will be explained below in greater detail, the manufacture of the universal low-profile intercranial assembly 10 utilizes computer-based designs of the mounting plate 12, the static cranial implant 16 and the functional neurosurgical implant 18. The computer-based designs of the mounting plate 12, static cranial implant 16 and the functional neurosurgical implant 18 are optimized during virtual design sessions incorporating neurosurgeon, plastic-reconstructive, or other surgeon input. The optimization process takes into account the three-dimensional, spatial relationship between the mounting plate 12, the static cranial implant 16 and the functional neurosurgical implant 18 (amongst one another if there is more than one functional neurosurgical implant 18), as well as the underlying topographical relationship of the mounting plate 12/static cranial implant 16/functional neurosurgical implant 18 with the brain-skull anatomy and physiology of the specific patient for whom the universal low-profile intercranial assembly 10 is being customized and manufactured. Modification of a digitally rendered mounting plate 112a and digitally rendered base static cranial implant 116a with a final shape and contour before sterilization and surgical implantation in accordance with the present invention (to produce the final mounting plate 12 and the final static cranial implant 16) results in the present low-universal low profile intercranial assembly 10. Through this process the spatial arrangement between the mounting plate 12, the low-profile static cranial implant 16 and the functional neurosurgical implant 18 is improved when placed within the confines of one's skull.

Figures 2, 3:
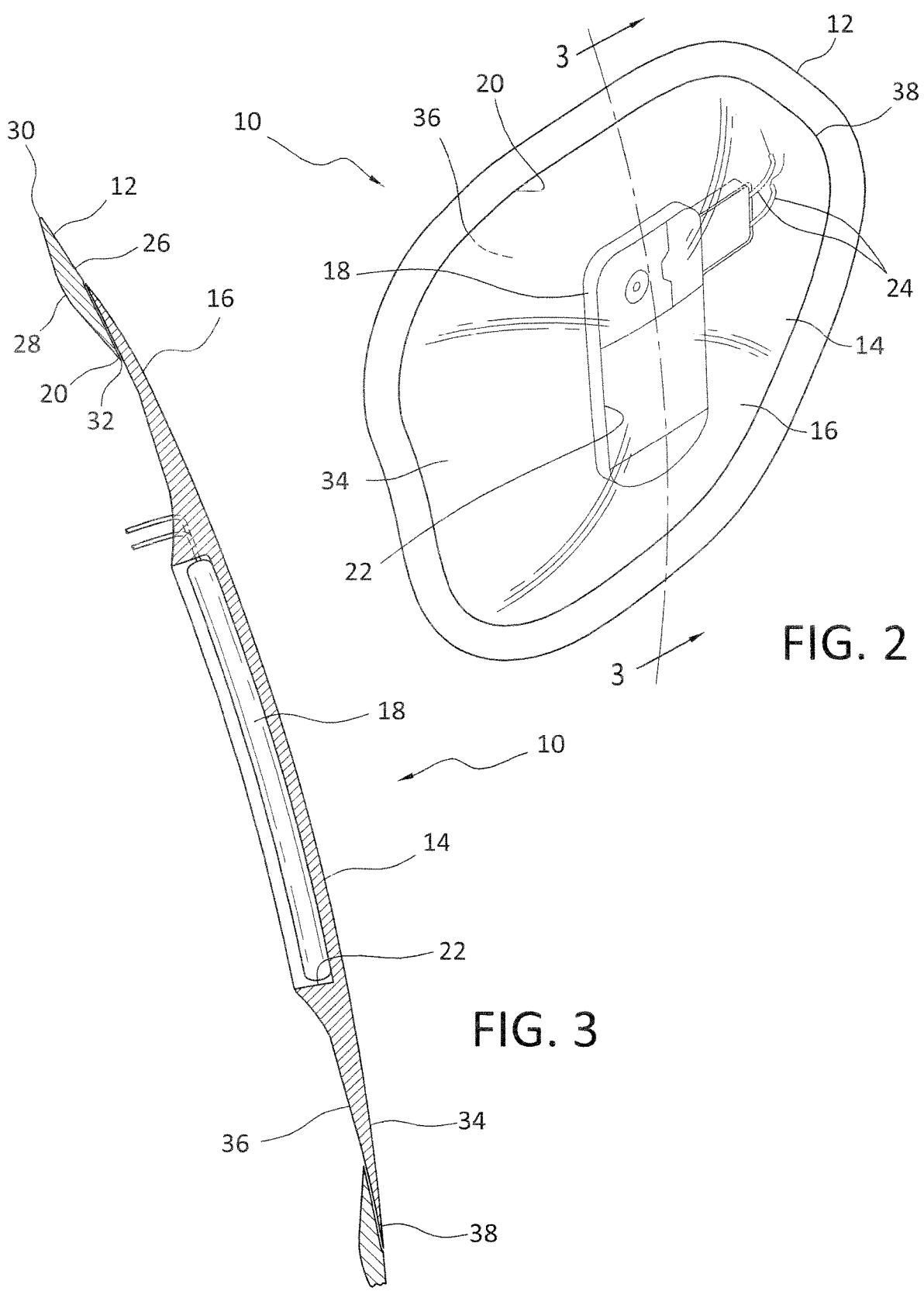
FIG. 2 is a perspective view of the universal low-profile intercranial assembly in accordance with a preferred embodiment of the present invention.
FIG. 3 is a sectional view of the universal low-profile intercranial assembly shown in FIG. 2.
Figures 17, 18:
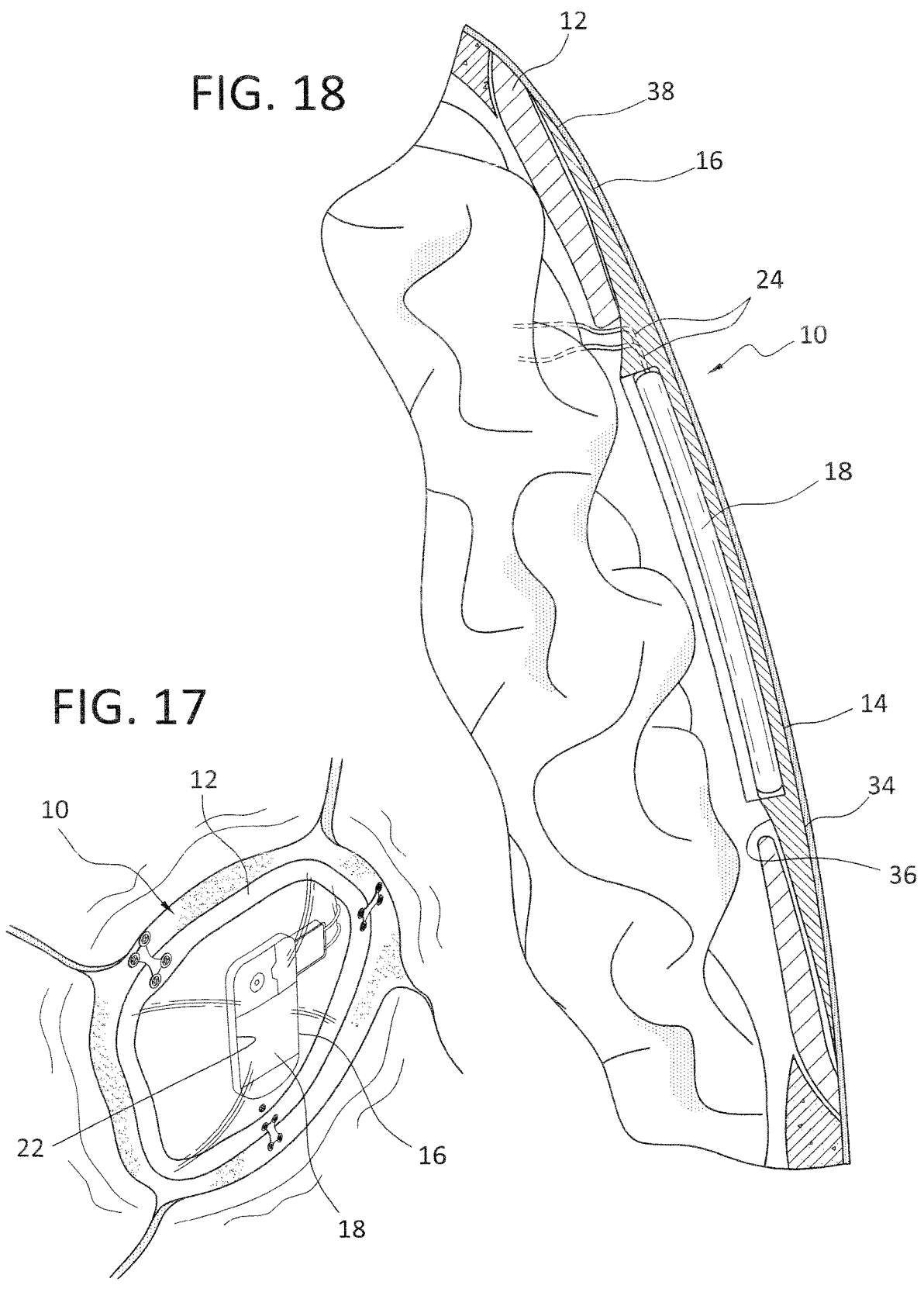
FIG. 17 is an installed perspective view of the universal low-profile intercranial assembly shown in FIG. 1.
FIG. 18 is a sectional view of the universal low-profile intercranial assembly shown in FIG. 17.
Figure 19:
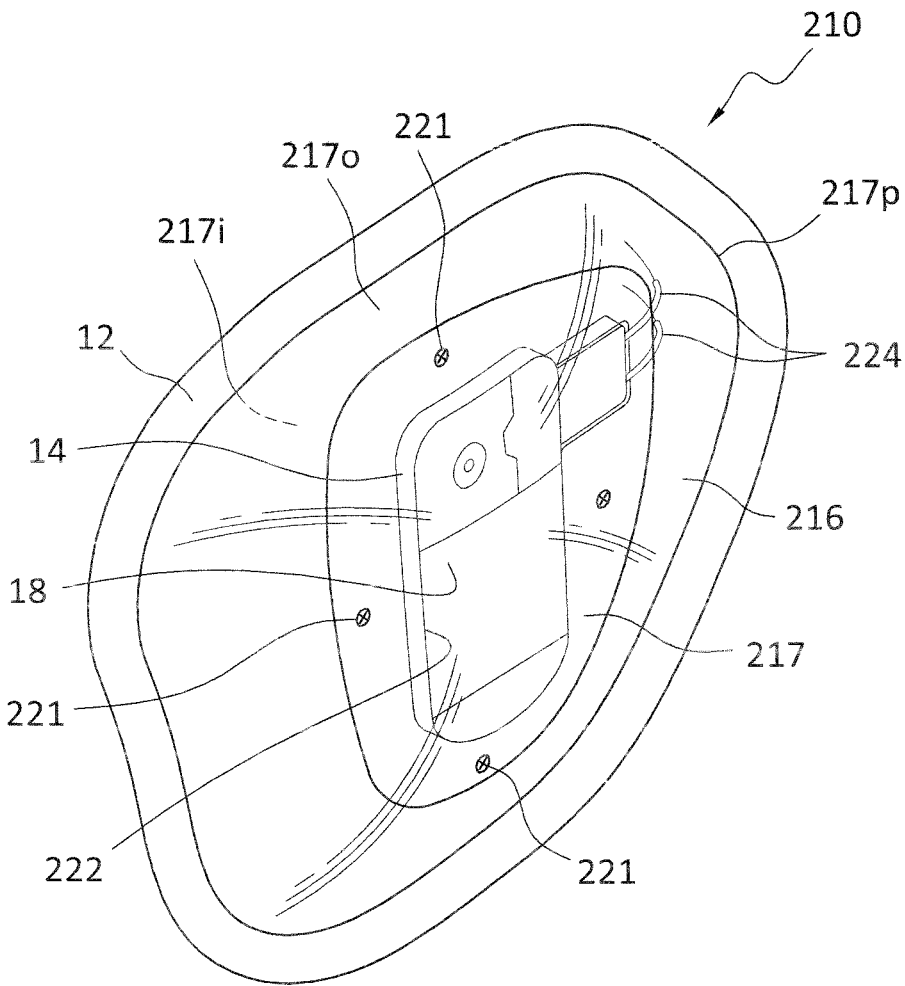
FIG. 19 is a perspective view of a universal low-profile intercranial assembly in accordance with an alternate embodiment wherein the customized static cranial implant is of a two-piece construction.
Figure 20:
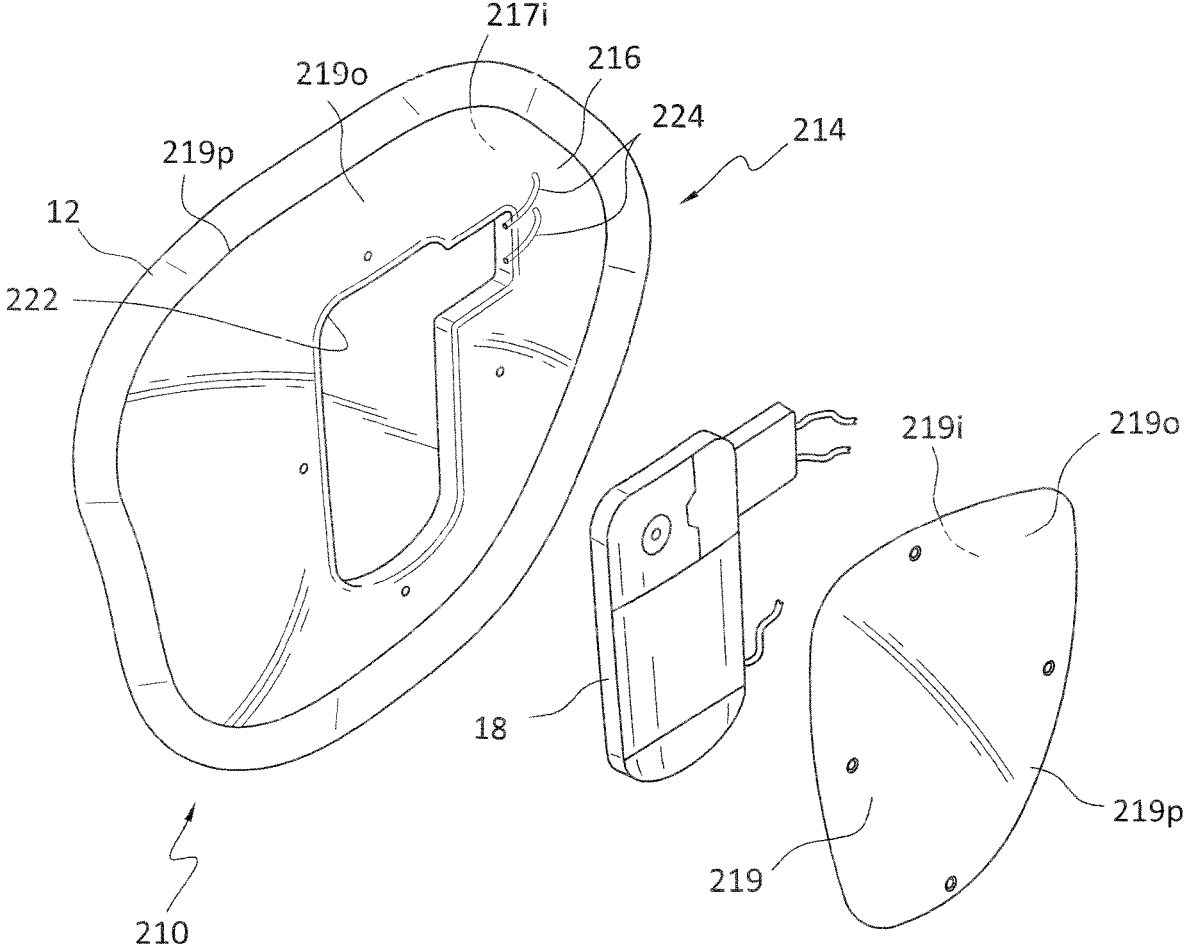
FIG. 20 is an exploded view of the universal low-profile intercranial assembly shown in FIG. 19.
Figures 21, 22:
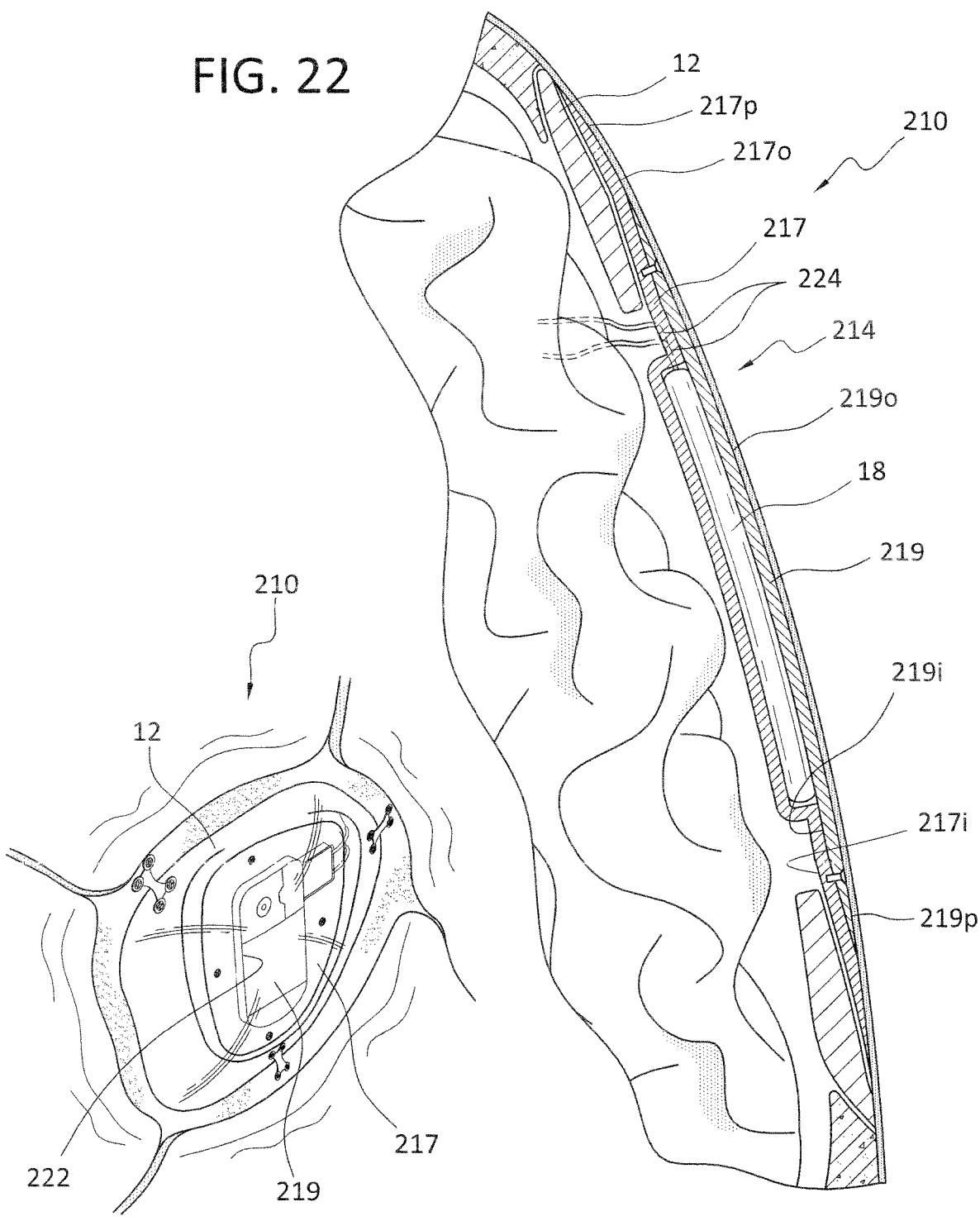
FIG. 21 is an installed perspective view of the universal low-profile intercranial assembly shown in FIG. 19.
FIG. 22 is a sectional view of the universal low-profile intercranial assembly shown in FIG. 21.

Considering now the structural details of the mounting plate 12, the mounting plate 12 includes an outer (commonly convex) first surface 26, an inner (commonly concave) second surface 28, and a peripheral edge 30 extending between the outer first surface 26 and the inner second surface 28. The mounting plate 12 is shaped and dimensioned for engagement with the skull of the patient upon implantation in a manner well known to those skilled in the field of neurosurgical procedures. The outer first surface 26 and inner second surface 28 of the mounting plate 12 are preferably curved in a superior to inferior direction, a posterior to anterior direction, and a medial to lateral direction. In addition, and as noted in the embodiments discussed with reference to FIGS. 3, 11, and 18, the peripheral edge 30 has a substantial taper for resting upon a matching taper formed along the skull. It is, however, appreciated that this taper may vary (or not exist at all, that is, the peripheral edge 30 may be substantially perpendicular relative to the outer first surface 26 and the inner second surface 28) depending upon the specific needs of the procedure. In accordance with a preferred embodiment, the mounting plate 12 will have a preselected thickness not exceeding the space between the inner surface of the scalp and the outer surface of the dura, for example, in the range of around 1 millimeter to 25 millimeters (with areas of strategic bulking and/or thinning) and depending upon the strength of the materials used in the construction of the mounting plate. Preferably, the mounting plate 12 will have a thickness of 1 millimeter to 12 millimeters. As mentioned above, the mounting plate 12 also includes a center aperture 20 designed to accommodate the static cranial implant 16. The center aperture 20 is defined by an inner wall 32 extending between outer first surface 26 and inner second surface 28 of the mounting plate 12.

In accordance with a preferred embodiment, the mounting plate 12 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, titanium alloy, allograft, autograft, xenograft, and/or various other tissue-engineered constructs. In accordance with one embodiment, the mounting plate 12 is ideally made of clear PMMA since it's fully lucent and transparent. As will be explained below in greater detail, the transparency also allows for the critical transmission of vital imaging with minimal distortion, such as ultrasound waves for brain pathology detection, and wireless signal communication (i.e., electroencephalography or ECOG)—essential for various neuromodulation devices such as NeuroPace®, for example. Another clear material that may be readily used in accordance with the present invention is cubic zirconium. While clear material is disclosed in accordance with a preferred embodiment, it is appreciated the underlying concepts of the present invention may be achieved through the utilization of an opaque mounting plate 12 as shown with reference to FIG. 10.

Still further, the mounting plate 12 is constructed of a material allowing for imaging of the brain through the mounting plate 12, for example, via ultra-sound. It is known that clear PMMA will provide the ability to permit ultrasound imaging of the brain therethrough so long as it is manufactured without additives that might function to block the radio waves of the imaging device.

Considering the static cranial implant 16 it should first be appreciated, the term "static" is used in the description of the present invention because the static cranial implant 16, has no encapsulated inner working (i.e., "functional") parts, batteries, wires, or computers, and is essentially an improved "empty-shell" which optimizes the inter-implant positioning within the confines of the skull and the neighboring functional neurosurgical implant 18.

Briefly, and as will be appreciated based upon the following disclosure, the static cranial implant 16 of the present invention is a modified version of a low-profile cranial implant commonly used and known by those skilled in the art of cranial surgical procedures. Such implants may take a variety of forms and are most commonly shaped and dimensioned for integration into the structure of a patient's skull; that is, the static cranial implant 16 has a geometry that substantially conforms to a resected portion of the patient's anatomy to which the implant is to be secured. Briefly, the static cranial implant 16 of the present invention includes an outer (commonly convex) first surface 34, an inner (commonly concave) second surface 36, and a peripheral edge 38 extending between the outer first surface 34 and the inner second surface 36. The static cranial implant 16 is shaped and dimensioned for engagement with the skull of the patient upon implantation in a manner well known to those skilled in the field of neurosurgical procedures. The outer first surface 34 and inner second surface 36 of the static cranial implant 16 are preferably curved in a superior to inferior direction, a posterior to anterior direction, and a medial to lateral direction. In addition, and as noted in the embodiments discussed with reference to FIGS. 3,11, and 18, the peripheral edge 38 has a substantial taper for resting upon a matching taper formed along the skull. It is, however, appreciated that this taper may vary (or not exist at all, that is, the peripheral edge 38 may be substantially perpendicular relative to the outer first surface 34 and the inner second surface 36) depending upon the specific needs of the procedure. In accordance with a preferred embodiment, the static cranial implant 16 will have a preselected thickness not exceeding the space between the inner surface of the scalp and the outer surface of the dura, for example, in the range of around 1 millimeter to 25 millimeters (with areas of strategic bulking and/or thinning) and depending upon the strength of the materials used in the construction of the static cranial implant 16. Preferably, the static cranial implant 16 will have a thickness of 1 millimeter to 12 millimeters.

As mentioned above, the static cranial implant 16 also includes a cavity 22 (for example, formed along the second inner surface 36) and optional structural elements 24, for example, tunnels, channels, pockets, access holes, and/or other structural elements, designed to accommodate various features of the functional neurosurgical implant 18. In the disclosed embodiment, structural elements 24 in the form of channels are provided. The channels 24 have a first end in communication with the center cavity 22 and a second end extending to the inner second surface 36 (or top surface) of the static cranial implant 16 for the passage of electrodes of the functional neurosurgical implant 18 for applying stimulation to the brain. As many functional neurosurgical implants 18 such as disclosed in FIGS. 1, 2, 3, 11, 12 and 14-18 interact with a control device (not shown) via wireless mechanisms, access between the outer first surface 34 and the center cavity 22 may not be required, although it is appreciated channels or other structural elements could certainly be provided for external contact as needed.

In accordance with a preferred embodiment, the static cranial implant 16 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, titanium alloy, allograft, autograft, xenograft, and/or various other tissue-engineered constructs. In accordance with one embodiment, the static cranial implant 16 is ideally made of clear PMMA since it's fully lucent and transparent. This allows for novel inspection of the interdigitated functional neurosurgical implant 14 and neighboring components. As will be explained below in greater detail, it also allows for the critical transmission of vital imaging with minimal distortion, such as ultrasound waves for brain pathology detection, and wireless signal communication (i.e., electroencephalography or ECOG)— essential for various neuromodulation devices such as NeuroPace®, for example. Another clear material that may be readily used in accordance with the present invention is cubic zirconium. While clear material is disclosed in accordance with a preferred embodiment, it is appreciated the underlying concepts of the present invention may be achieved through the utilization of an opaque static cranial implant 16 as shown with reference to FIG. 10.

The optical clarity of the static cranial implant 16 is important in expanding the potential uses of the universal low-profile intercranial assembly 10 and in expanding the potential functional neurosurgical implants 18 that may be used in conjunction with the present invention. For example, the provision of high optical clarity allows for wireless optical links between the functional neurosurgical implants

18 and remote devices or between functional devices on the interior of the cranium and the exterior of the universal low-profile intercranial assembly 10 (for example, transmitting between the cortex and the other side of the low-profile intercranial device 14). Enhanced optical clarity similarly allows for power transmission and/or receipt between the functional neurosurgical implants 18 and devices outside of the static cranial implant 16. Potential operations that may be achieved through the utilization of optical links through a high clarity static cranial implant 16 include, but are not limited to, device start-up, device calibration, and device operational control.

Still further, the static cranial implant 16 is constructed of a material allowing for imaging of the brain through the static cranial implant 16, for example, via ultra-sound. It is known that clear PMMA will provide the ability to permit ultra-sound imaging of the brain therethrough so long as it is manufactured without additives that might function to block the radio waves of the imaging device. In addition, and with reference to FIG. 11, the static cranial implant 16 may include an embedded antibiotic (shown as little dots), which is mixed with the polymer from which the static cranial implant 16 is made, to help reduce the risk of acute or chronic infections from occurring.

Figures 10, 11, 12, 13:
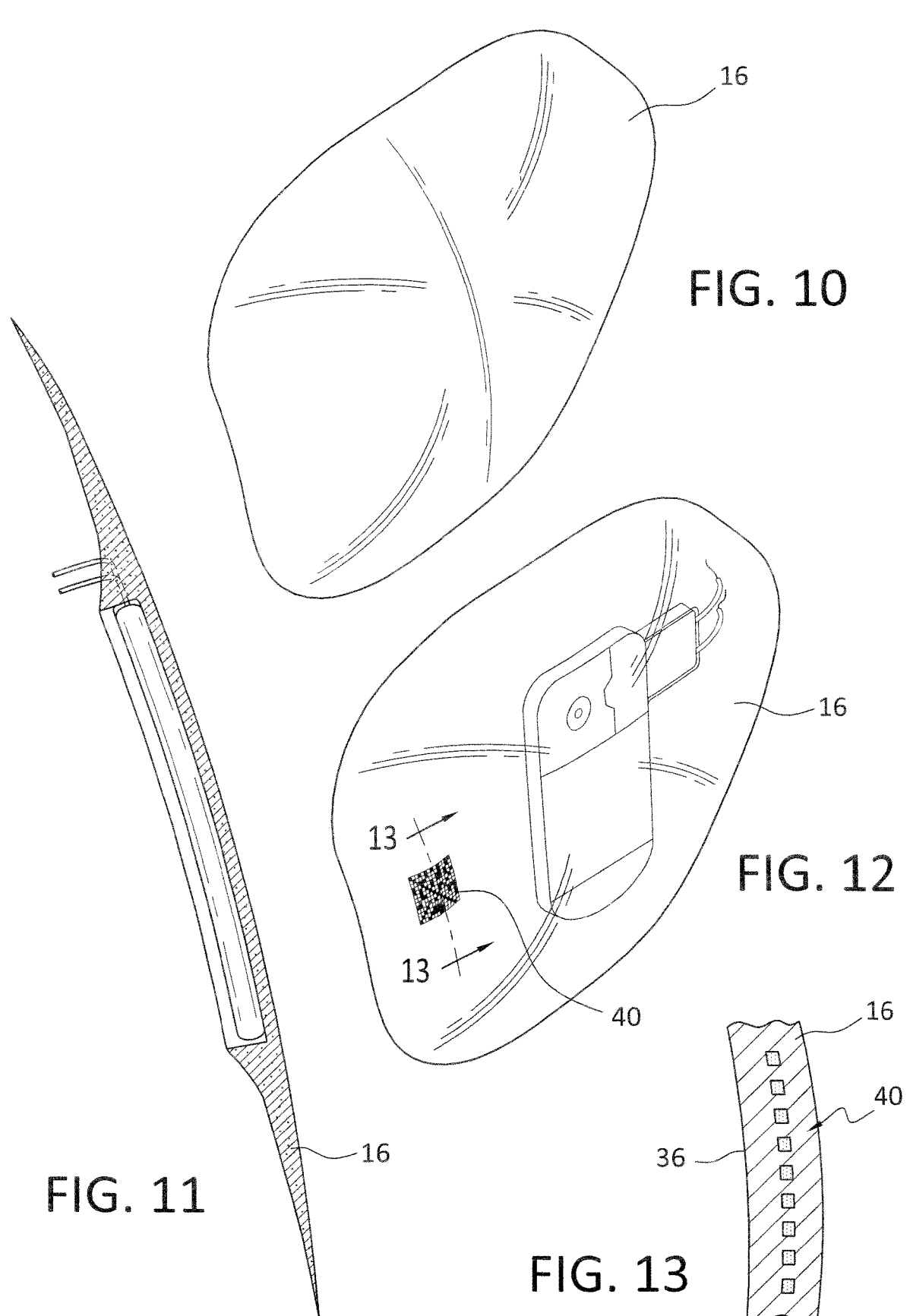
FIG. 10 is a perspective view of an opaque customized static cranial implant in accordance with an alternate embodiment of the present invention.
FIG. 11 is a cross sectional view of a low-profile intercranial device showing a customized static cranial implant fabricated with embedded antibiotics in accordance with an alternate embodiment of the present invention.
FIG. 12 is a perspective view of a low-profile intercranial device including a customized static cranial implant with an embedded serial number in accordance with an alternate embodiment of the present invention.
FIG. 13 is a cross sectional view along the line 13-13 in FIG. 12.

With reference to FIGS. 12 and 13, the static cranial implant 16 may also be provided with an embedded serial number (or implant identifier) 40 that is viewable via CT or MRI (Magnetic Resonance Imaging) scan. In accordance with a preferred embodiment, such embedded serial numbers will be positioned along the inner second surface 36 of the static cranial implant 16. The embedded serial number 40 is preferably in the form of a QR (Quick Response) Code, that is, a two dimensional barcode offering enhanced patient privacy, ready readability, and vast versatility. The embedded serial number 40 is achieved by integrating various materials that are viewable via CT or MRI scan into the base material of the static cranial implant 16. For example, the materials may be barium sulfate or zirconium dioxide integrated into the static cranial implant 16 so as to function as a serial number that may be viewed after implant.

As shown with reference to FIG. 14, the static cranial implant 16 is also preferably constructed with alignment markings 42a, 42b. In accordance with a preferred embodiment, the alignment markings 42a, 42b run fully across the static cranial implant 16 and are formed in the shape of a cross. As such, the alignment markings include a first alignment marking 42a formed upon the static cranial implant 16 to identify the superior to the inferior direction of the universal low-profile intercranial assembly 10 when properly implanted, and a second alignment marking 42b formed upon the static cranial implant 16 necessary to identify the posterior to anterior direction of the low-profile intercranial device 14 when properly implanted. These alignment markings 42a, 42b are preferably formed via laser etching of the static cranial implant as the static cranial implant 16 is fabricated for use in accordance with the present invention. The laser etching may be combined with CNC (Computer Numerically Controlled) techniques to optimize the accuracy of markings or other known marking techniques may be employed were they offer sufficient accuracy to warrant use in accordance with the present invention.

The mounting plate 12 of the present invention may be provided with relief recesses 44 (see FIG. 15) for the creation of a perfectly smooth surface when titanium plates are utilized in conjunction with the universal low-profile intercranial assembly 10 for securing the universal low-profile intercranial assembly 10 in a desired position. In accordance with such an embodiment, the relief recesses are 0.4 mm in depth as titanium plates are known to be very thin.

Still further, and with reference to FIG. 16, the customize static cranial implant 16 may be provided with laser cut lines 46 identifying cuts for various other devices that may be utilized in conjunction with the low-profile intercranial device 14. For example, the laser cut lines 46 might identify the location of a NeuroPace® neurostimulator device positioned adjacent to the low-profile intercranial device 14. Still further, the laser cut lines 46 may be utilized for providing insight into the desired location of the low-profile intercranial device 14.

In addition to laser cut lines, laser markings 48 maybe made along the outer first surface 34 or inner second surface 36 of the static cranial implant 16 to provide an indication of critical anatomy relating to the installation of the universal low-profile intercranial assembly 10 in accordance with the present invention. For example, such laser markings 48 might be useful in identifying critical neuro anatomy relating to the functional neurosurgical implant 18 of the low-profile intercranial device 14.

While a preferred static cranial implant 16 is disclosed in accordance with the present invention, the static cranial implant 16 used in conjunction with the present invention may take a variety of forms so long as the static cranial implant includes a center cavity (and, optionally, other structural elements) configured to conform to the exact requirements of the functional neurosurgical implant in accordance with the present invention. For example, the cranial implant might take the form of a cranial device as disclosed in PCT Publication No. WO 2017/039762, entitled "LOW-PROFILE INTERCRANIAL DEVICE," filed May 2, 2016, which is incorporated herein by reference.

While a one-piece construction for the static cranial implant is disclosed above, multiple-piece constructions are contemplated in accordance with the present invention. For example, and with reference to FIGS. 19-22, the static cranial implant 216 may have a two-piece construction allowing for ready access to the functional neurosurgical implant 218 without the need for complete removal of the low-profile intercranial device 214. As with the embodiment described above, the two-piece static cranial implant 216 has no encapsulated inner working parts, batteries, wires, or computers, and is essentially an improved "empty-shell."

The two-piece static cranial implant in accordance with this embodiment includes a base cranial implant member 217 and a cover cranial implant member 219. The base cranial implant member 217 has a geometry that substantially conforms to a resected portion of the patient's anatomy to which the low-profile intercranial device is to be secured. The base cranial implant member 217 includes an outer (commonly convex) first surface 217o, an inner (commonly concave) second surface 217i, and a peripheral edge 217p extending between the outer first surface 217o and the inner second surface 217i. The static cranial implant 216 is shaped and dimensioned for engagement with the skull of the patient upon implantation in a manner well known to those skilled in the field of neurosurgical procedures. The outer first surface 217o and inner second surface 217i of the base cranial implant member 217 are preferably curved in a superior to inferior direction, a posterior to anterior direction, and a medial to lateral direction.

The base cranial implant member 217 also includes a center recess 222 formed along the outer first surface 217o and optional structural elements 224, for example, tunnels, channels, pockets, access holes, and/or other structural elements, designed to accommodate various features of the functional neurosurgical implant. As with the prior embodiment, multiple recesses may be employed where the functional neurosurgical implant(s) 218 being used dictates and that the recess 222 need not be directly in the center of the base cranial implant member 217 but may be offset as dictated by the procedure being performed.

In accordance with a preferred embodiment, the base cranial implant member 217 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, titanium alloy, and/or various other tissue-engineered constructs. In accordance with one embodiment, the base cranial implant member 217 is ideally made of a clear PMMA since it's completely transparent and fully lucent. This allows for novel inspection of the interdigitated functional neurosurgical implant and neighboring components.

In addition to the base cranial implant member 217, the two-piece static cranial implant 216 includes a cover cranial implant member 219. The cover cranial implant member 219 is shaped and dimensioned for positioning over the center recess 222 along the outer first surface 217o of the base cranial implant member 217. In accordance with a preferred embodiment, the cover cranial implant member 219 is secured to the base cranial implant member 217 by screw 221 fixation. The cover cranial implant member 219 includes an outer (commonly convex) first surface 219o, an inner (commonly concave) second surface 219i, and a peripheral edge 219p shaped and dimensioned for engagement with the outer first surface 217o of the base cranial implant member 217 along the periphery of the center recess 222. As with the base cranial implant member 217, the outer first surface 219o and inner second surface 219i of the cover cranial implant member 219 are preferably curved in a superior to inferior direction, a posterior to anterior direction, and a medial to lateral direction.

The base cranial implant member 217 and the cover cranial implant member 219 have a total thickness similar to that of the embodiment described above, that is, and depending on the strength characteristics of the materials used, the base cranial implant member 217 and the cover cranial implant member 219 will have a thickness (with areas of strategic bulking and/or thinning) of around 1 millimeter to 25 millimeters, preferably, 1 millimeter to 12 millimeters.

As mentioned above, the cover cranial implant member 219 fits over the center recess 222 along the outer first surface 217o of the base cranial implant member 217. In this way, the inner second surface 219i of the cover cranial implant member 219 and the outer first surface 217o of the base cranial implant member 217, along the center recess 222, define a center cavity 223 configured to conform to the exact requirements of the functional neurosurgical implant 218 in accordance with the present invention. With this in mind, the inner second surface 219i of the cover cranial implant member 219 may be shaped and/or contoured to enhance the positioning of the functional neurosurgical implant 218 within the center cavity 223.

The functional neurosurgical implant 18 of the present invention is selected from a variety of FDA-approved and experimental options for electrical, optical, mechanical, medicinal and other treatment/monitoring devices designed for long term invasive treatment and/or disease-monitoring of patients requiring such attention. These functional neurosurgical implants 18 are known devices manufactured by various vendors within the neurosurgical industry and have known, unmodifiable dimensions that may be used in the modification of the static cranial implant to optimize surgical results by minimizing abnormal shapes, visible contours, and/or craniofacial deformities.

Based upon the functional neurosurgical implant 18 used in conjunction with the present invention, the functional neurosurgical implant may be useful in the treatment of various patient conditions such as epilepsy, movement disorders, chronic pain, spasticity, cerebral palsy, multiple sclerosis, spinal cord injury, traumatic brain injury, attention-deficit/hyperactivity disorder, autism, etc.—and the potential to obtain supra-normal levels of brain function in both military and civilian situations. Furthermore, incorporation of imaging devices within cranial implants could help to provide ongoing tumor bed monitoring for early detection of disease recurrence.

By way of example, one potential functional neurosurgical implant 18 that may be employed in accordance with the present invention is a battery-powered functional neurosurgical implant known as the NeuroPace® device, that is, a device for responsive neurostimulation for epilepsy, which has a design flaw in that it limits the visible aesthetic result due to its irregular shape(s), requires placement of battery(ies) within the chest with wires going along the neck, and suffers from high rates of implant micromotion thereby leading to common device infection and bone flap osteomyelitis (See, Wei Z, Gordon C R, Bergey G K, Sacks J M, Anderson W S. Implant Site Infection and Bone Flap Osteomyelitis Associated with the NeuroPace Responsive Neurostimulation System. World Neurosurg 2015 Dec. 29; pii: s1878-8750(15)01775-1.) These deficiencies are overcome in accordance with the present invention by optimizing the static cranial implant for receipt of the NeuroPace® device.

With the foregoing in mind, additional functional neurosurgical implants that may be used in conjunction with the present invention include, but are not limited to the following: Deep Brain Stimulators (DBS); Cortical Brain Stimulators (CBS); neurologic medicines that are otherwise prevented from diffusing through the blood-brain barrier via common delivery methods; battery/passively/kinetically/or otherwise-powered functional devices including neuromodulation devices, imaging devices, radiation therapy devices, and remote sensing/monitoring devices; monitoring devices for abnormal levels of intracranial pressure (ICP) or brain activity (i.e., seizures), such as an electrical array for motor/vision cortex control, battery/passively/kinetically/or otherwise-based stimulation hardware for epilepsy management (grids/batteries/wires); low-profile remote imaging devices (e.g., optical coherence tomography (OCT), duplex ultrasound); delivery/sensing devices for electrical impulses; neurological and physiological systems required for deep space/sleep functionalities enhancing the monitoring and/or maintenance of bodily vital signs, nutrition, cognition, etc.; convection enhanced delivery systems effectively delivering therapeutics to substantial volumes of brain and brain tumor; and remote neuro-imaging devices (i.e., electroencephalogram (EEG).

The functional neurosurgical implants of the present invention may also incorporate high-precision and fully implantable next-generation neural interface systems taking advantage of microelectronics and photonics along with advances in scalable neural encoding and processing algorithms to demonstrate the transformation of high-definition sensory stimuli to and from sensory cortex areas, bridging physiological and electronic neural activity representations.

With this in mind, the term "functional neurosurgical implant" is meant to reference any therapeutic hardware or compositions including, but not limited to, medicines to treat any patient-specific illness, or electronic, mechanical, imaging modality, cerebral spinal fluid (CSF) shunting, and/or electro-mechanical device to remotely monitor (e.g., via Wi-Fi connectivity) or intervene any specific neurologic illness, including imaging, monitoring, electrostimulation, radiation therapy, polarized light/laser neuronal modulation devices. The term "functional" denotes the fact that these implants provide the universal low-profile intercranial assembly with the ability to function as more than a safe custom-shaped skull replacement by providing various functionalities, for example, local drug delivery, monitoring (such as brain monitoring), or local electric stimulation to the patient.

Figure 4:
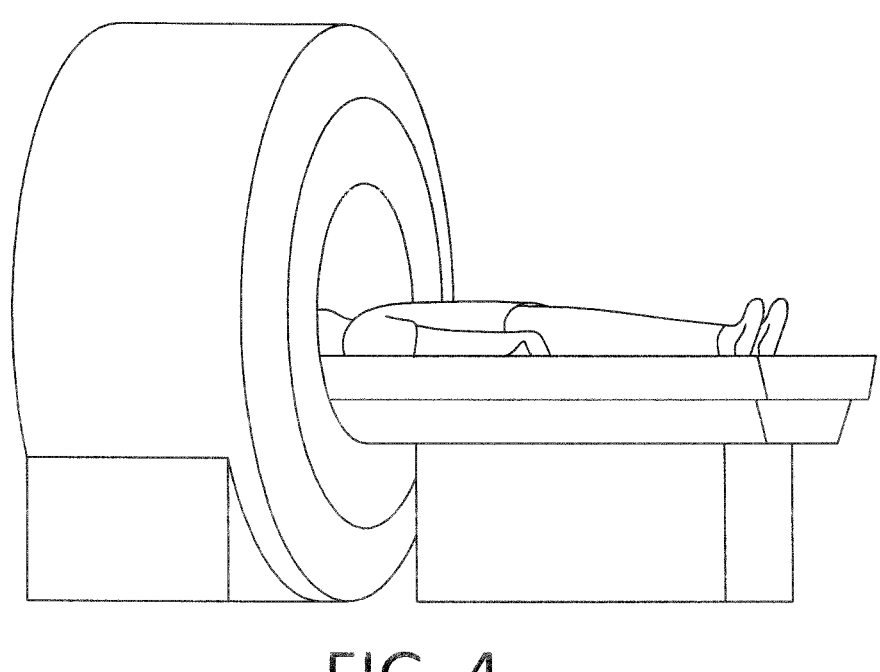
FIG. 4 shows a patient obtaining a protocol CT scan prior to surgery.

The following describes the steps employed in the manufacture and installation of the universal low-profile intercranial assembly 10 of the present invention. While the procedure is described for manufacture and installation of the one—piece customized static cranial implant 16, the two-piece static cranial implant 216 is processed in the same manner. After the patient is diagnosed as requiring the implantation of a low profile intercranial device 14 as a replacement for a specific portion of the cranium (either to reconstruct a portion of the cranium or to replace a surgeon created defect) in accordance with the claimed invention, the patient first undergoes a high-definition, protocol CT scan of his or her head prior to surgery (which is customary for all neurosurgical patients in need of cranial implants) (see FIG. 4) and the CT scan is then converted to an STL file (or other digital data format useful in computer-assisted design/computer-assisted manufacture (CAD/CAM) manufacture procedures) (see FIG. 5).

Figure 5:
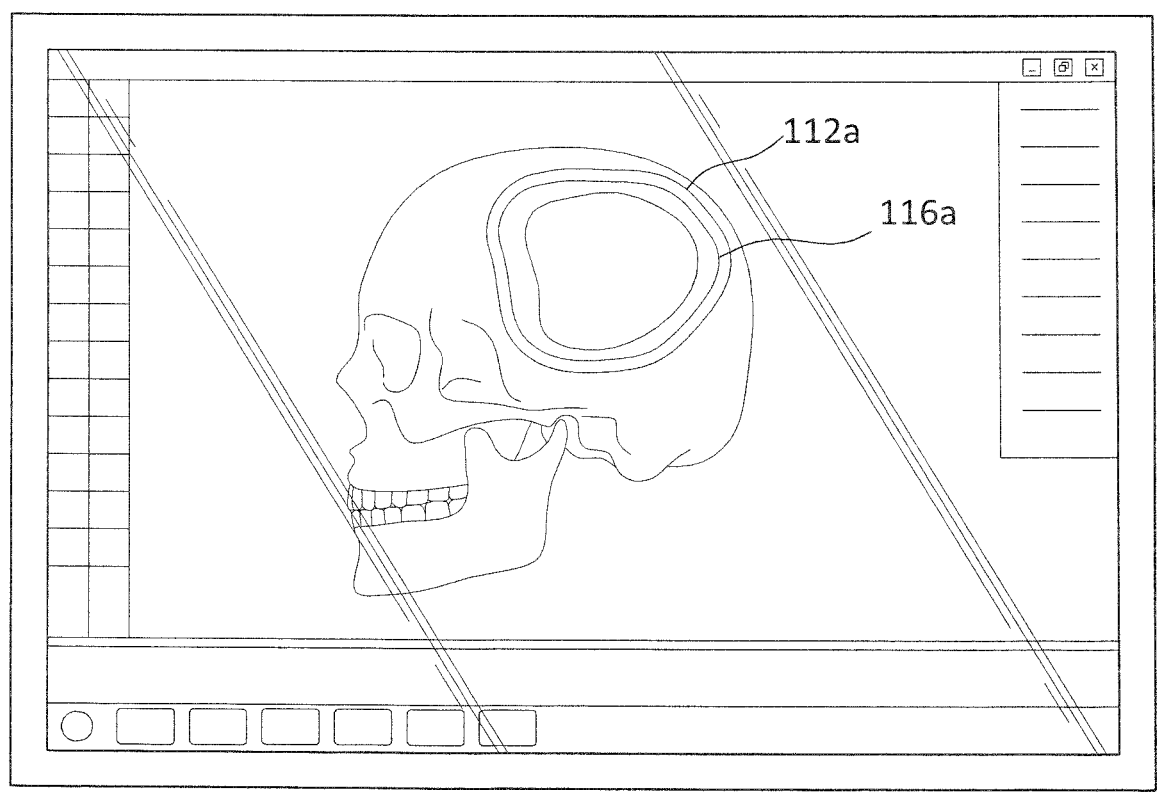
FIG. 5 shows the CT scan is then converted to a digital data format useful in computer-assisted design/computer-assisted manufacture (CAD/CAM) manufacture procedures.
Figure 6:
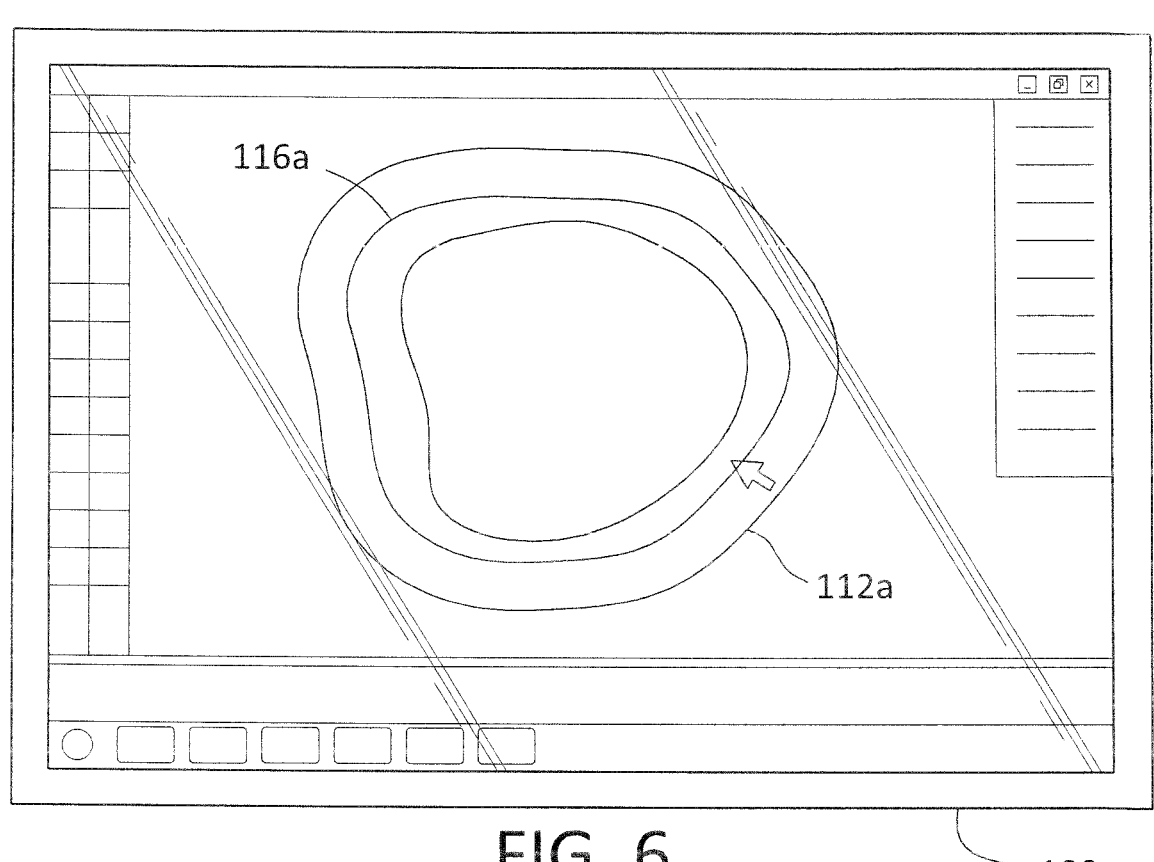
FIG. 6 is a computer screenshot showing a digitally rendered mounting plate and a digitally rendered base static cranial implant in accordance with the present invention.

With the STL file of the CT scan completed, the digital image of the patient (for those patients either with or without an existing skull defect) is used by a design engineer to create a digitally rendered mounting plate 112a and a digitally rendered base static cranial implant 116a using conventional computer-assisted design (CAD)/computer-assisted modeling (CAM) techniques (See FIGS. 5 and 6). Feedback from a surgeon(s) pre-operatively helps to reveal any unexpected surgical details and aids one in confirming an ideal, planned location of functional neurosurgery and relevant topographical brain anatomy underneath the planned low-profile intercranial device. It is appreciated the CAD/CAM techniques, as well as other automated elements of the present methodology are accomplished using conventional computer and technology equipment 100 well known to those skilled in the art. The digitally rendered mounting plate 112a and the digitally rendered base static cranial implant 116a exhibit shapes exact to the size, thickness, and contour of the patient's unique cranium. The digitally rendered mounting plate 112a and the digitally rendered base static cranial implant 116a are then stored as an STL file (or other digital data format useful in computer-assisted design manufacture procedures).

Figure 7:
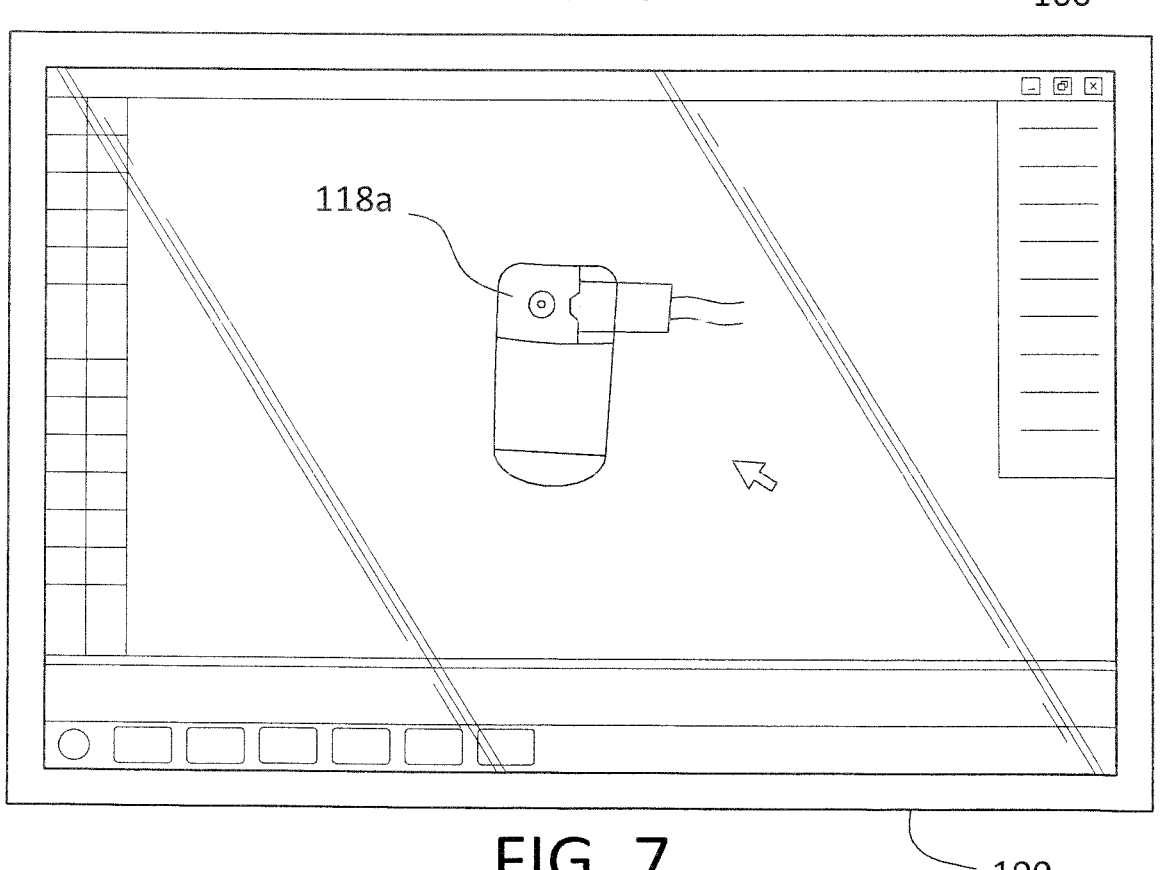
FIG. 7 is a computer screenshot showing a digitally rendered functional neurosurgical implant in accordance with the present invention.

Simultaneously, before or after the creation of the digital design of the cranial implant, a digital rendering of the functional neurosurgical implant ("digitally rendered functional neurosurgical implant 118a") to be used with the static cranial implant is created (or obtained from the third party vendor responsible for the manufacture of the functional neurosurgical implant (See FIG. 7). As with the digitally rendered mounting plate 112a and the digitally rendered base static cranial implant 116a, the digitally rendered functional neurosurgical implant 118a is stored as an STL file (or other digital data format useful in computer-assisted design manufacture procedures) commonly used by design engineers using (CAD)/(CAM) techniques and, as explained below, the exact dimensions of the functional neurosurgical implant are incorporated into the final universal low-profile intercranial assembly of the present invention.

Figure 8:
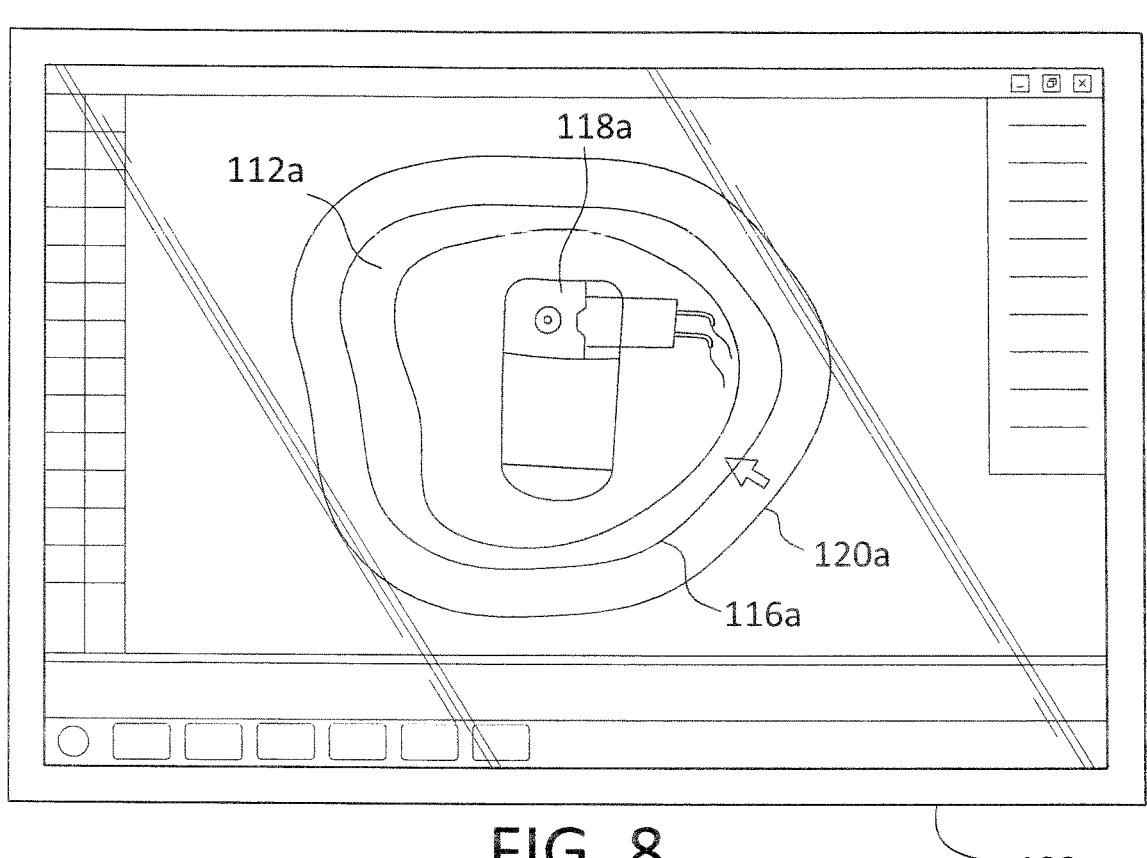
FIG. 8 is a computer screenshot showing a hybrid rendering in accordance with the present invention.

The digitally rendered functional neurosurgical implant 118a is then superimposed on the digitally rendered base static cranial implant 116a and the digitally rendered mounting plate 112a to produce a hybrid rendering including the digitally rendered mounting plate 112a, the digitally rendered functional neurosurgical implant 118a and the digitally rendered base static cranial implant 116a (see FIG. 8). It is appreciated multiple digital renderings of functional neurosurgical implants will be created and superimposed where the planned universal low-profile intercranial assembly includes multiple functional neurosurgical implants. With the digitally rendered functional neurosurgical implant 118a superimposed on the digitally rendered base static cranial implant 116a and the digitally rendered mounting plate 112a as a single superimposed digital drawing (that is, the hybrid rendering), the functional neurosurgical implant, the cranial implant and mounting plate (that is, the digitally rendered versions of both) may be optimized with patient-specific independent width/height/length dimensions to optimize anatomical harmony amongst the functional neurosurgical implant, the static cranial implant, and the mounting plate prior to surgery and allow virtual planning for the seamless integration of the functional neurosurgical implant, the static cranial implant, and the mounting plate. This optimization process results in the optimized hybrid rendering, composed of an optimized digitally rendered functional neurosurgical implant 118b, the optimized digitally rendered static cranial implant 116b, and the optimized mounting plate 112b as shown in FIG. 9.

Figure 9:
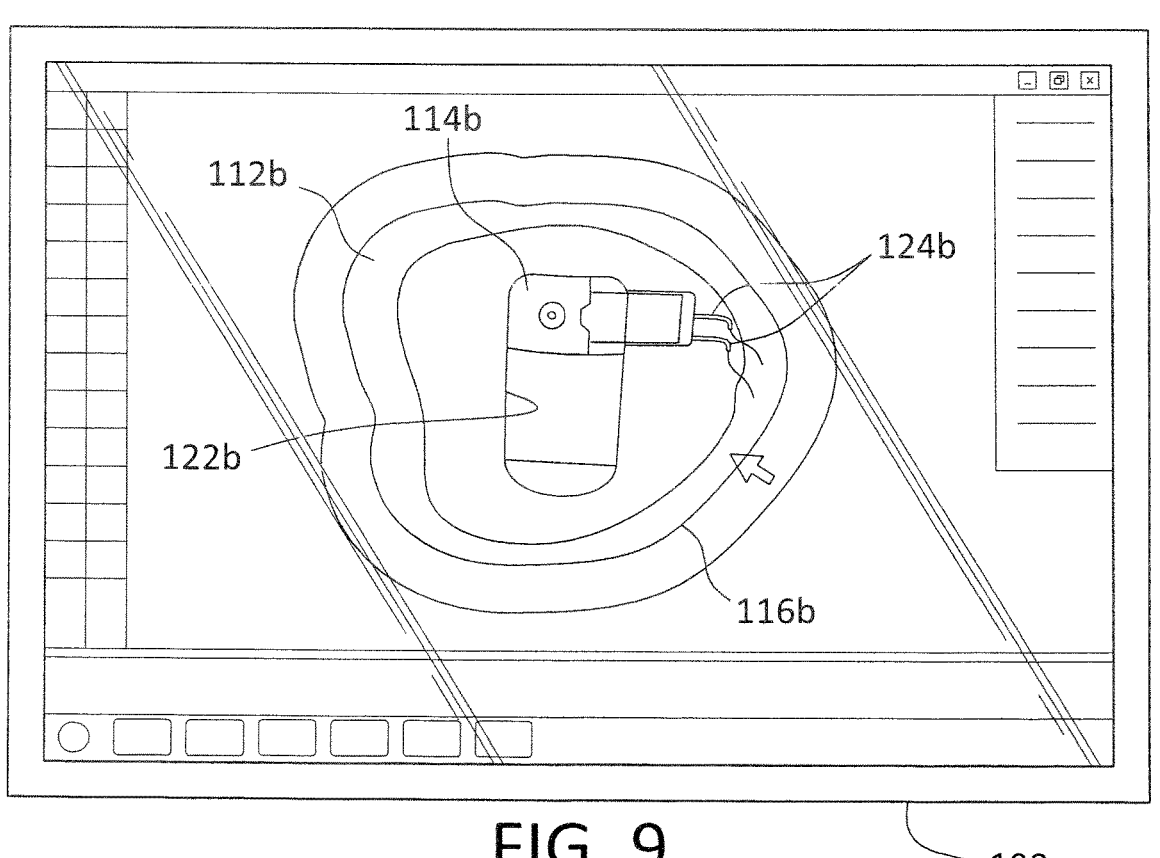
FIG. 9 is a computer screenshot showing an optimized hybrid rendering in accordance with the present invention.

As shown in FIG. 9, the optimized digitally rendered mounting plate 112b, digitally rendered functional neurosurgical implant 118b, and the optimized digitally rendered static cranial implant 116b are optimized such that the final components will have a "key-in-lock" type (that is, a closely conforming or high tolerance) fit. This optimization results in the optimized hybrid rendering composed of the optimized digitally rendered mounting plate 112b, the optimized digitally rendered functional neurosurgical implant 118b and the optimized digitally rendered static cranial implant 116b.

The optimized hybrid rendering offers both pre-operative virtual assessment of the relationship optimized digitally rendered mounting plate 112b, the optimized digitally rendered static cranial implant 116b, and the optimized digitally rendered functional neurosurgical implant 118b, as well as pre-operative optimization of the physical universal low-profile intercranial assembly 10 via known laser-cutting devices facilitated via surgical robot-assisted technologies (or by hand where such capabilities are not available). Both steps help to strengthen the chances that the relationship of mounting plate 12, static cranial implant 16, and the functional neurosurgical implant 18 will be optimized down to submillimeter accuracy. Depending upon the needs of the patient, the structure of the optimized digitally rendered mounting plate 112b, the optimized digitally rendered static cranial implant 116b, and the optimized digitally rendered functional neurosurgical implant 118b, the optimized digitally rendered mounting plate 112b, the optimized digitally rendered static cranial implant 116b, and the optimized digitally rendered functional neurosurgical implant 118b (as well as the resulting universal low-profile intercranial assembly 10 produced as a result of these renderings) will likely have many desired features (for improved safety and aesthetic outcomes relative to the patient appearance).

Once the optimized digitally rendered mounting plate 112b, the optimized digitally rendered static cranial implant 116b, and the optimized digitally rendered functional neurosurgical implant 118b are virtually matched, the anatomical aspects will be ideal for patient-specific needs and the optimized hybrid rendering (saved as an STL (or other digital format)) file is then used to manufacture the present universal low-profile intercranial assembly 10 which may ultimately be assembled.

In particular, with the STL (or other digital format) file of the optimized digitally rendered mounting plate 112b, the optimized digitally rendered static cranial implant 116b, and the optimized digitally rendered functional neurosurgical implant 118b, conventional manufacturing techniques are used to fabricate and laser cut the mounting plate 12, static cranial implant 16 and the functional neurosurgical implant 18 (to the extent necessary) with robot-assistance for extreme accuracy (see PCT Publication No. WO 2016/086049, based upon PCT Application No. PCT/US2015/62516, entitled "A CUTTING MACHINE FOR RESIZING RAW IMPLANTS DURING SURGERY"), as compared to commonly-employed, human hand modification. For example, the mounting plate 12 and the static cranial implant 16 can be obtained in "non-sterile form" from any of the dozens of FDA-approved companies in existence nationwide that are capable of producing cranial implants in accordance with the requirement of the optimized digitally rendered mounting plate and the optimized digitally rendered static cranial implant, respectively. A functional neurosurgical implant 18 corresponding to the optimized digitally rendered functional neurosurgical implant 18 may be purchased from appropriate vendors with or without FDA approval.

Figure 23:
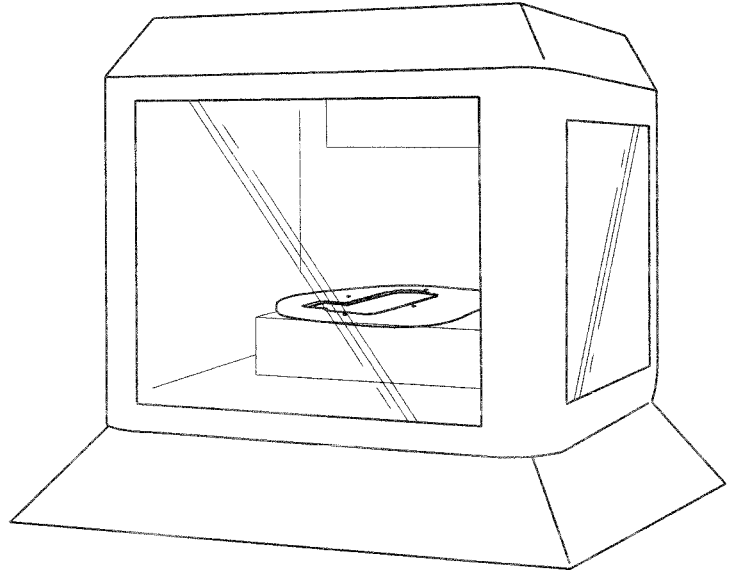
FIG. 23 is a perspective view of a 3-D printer that may be used in accordance with the present invention.

It is also appreciated that the mounting plate 12, static cranial implant 16, and/or the functional neurosurgical implant 18 may be produced through the use of 3-D digital printing technology (see FIG. 23). With this in mind, and in addition to distinctly separate functional neurosurgical implants, the functional neurosurgical implant 18 or portions thereof may be integrated into the static cranial implant 16 through three-dimensional printing. With the use of three-dimensional printing electronic circuitry employed by the functional neurosurgical implant 18 may be created directly on the surfaces of the static cranial implant 16 in a manner optimally utilizing the space available for the remaining portions of the functional neurosurgical implant 18. Similarly, vital nervous system components may be printed into the static cranial implant 16 or non-clear bony structures designed to resolve complex disabilities may be printed into the static cranial implant 16. For example, the functional neurosurgical implant 18 or portions thereof may be three-dimensionally printed within the center cavity 22. Where the two-piece embodiment as described above is employed, the functional neurosurgical implant 18 or portions thereof may be three-dimensionally printed on the center recess 222 of the base cranial implant member 217 or the cover cranial implant member 219. In another embodiment, the cranial implant 216 and the printable components of the functional neurosurgical implant 218 may be printed in a single print process taking advantage of the three-dimensional printing system's ability to print multiple materials during a single print job. Ultimately, the application of three-dimensional printing in accordance with the present invention allows immensely complex systems to be compacted into the space needed in the replacement of cranial bones.

By manufacturing the present universal low-profile intercranial assembly in this manner, the final physical components of the low-profile intercranial assembly 10, 210 that is, the mounting plate 12, the static cranial implant 16, 216 and the functional neurosurgical implant 18, are virtually matched pre-operatively such that the resulting universal low-profile intercranial assembly 10, 210 is ideally constructed to drastically minimize the risk of scalp pain, scalp contour irregularities, extrusion of implant through scalp, painful scalp syndrome, visual craniofacial deformity, and infection secondary to micromotion of foreign materials, and/or brain injuries when being placed underneath the skull.

With the universal low-profile intercranial assembly 10, 210 fully fabricated, the mounting plate 12 is positioned within the intercranial space so as to replace a portion of the resected portion. Thereafter, the static cranial implant 16, 216 and the functional neurosurgical implant 18 are positioned within the center aperture 20 of the mounting plate 12 so as to fully replace the resected portion of the cranium. In accordance with a preferred embodiment, the static cranial implant 16, 216 is secured within the center aperture 20 using standard fixation plates and screws made of titanium, although it is appreciated other mechanisms for rigid fixation, for example, tongue and groove coupling structures, wires, sutures, etc., may be employed in securely positioning the static cranial implant.

As briefly mentioned above, if it is desired later in the treatment of the patient to replace the functional or structural aspects of the universal low-profile intercranial assembly 10, 210 the static cranial implant 16, 216 and the functional neurosurgical implant 18 may be removed while the mounting plate 12 is left in position. Thereafter, another low profile intercranial device 14 may be constructed and positioned with the center aperture 20 of the mounting plate 12.

In accordance with a further feature of the present invention, and regardless of which embodiment is being implemented, the mounting plate and/or the static cranial implant may be provided with topographical markings allowing a surgeon to readily and accurately appreciate the thickness of the mounting plate and/or the static cranial implant at specific locations. This is especially important when one considers the transparent nature of the mounting plate and/or the static cranial implant as the transparency allows surgeon to see directly through the mounting plate and/or the static cranial implant but the material might distort the view as the surgeon looks through the mounting plate and/or the static cranial implant.

Figure 24A:
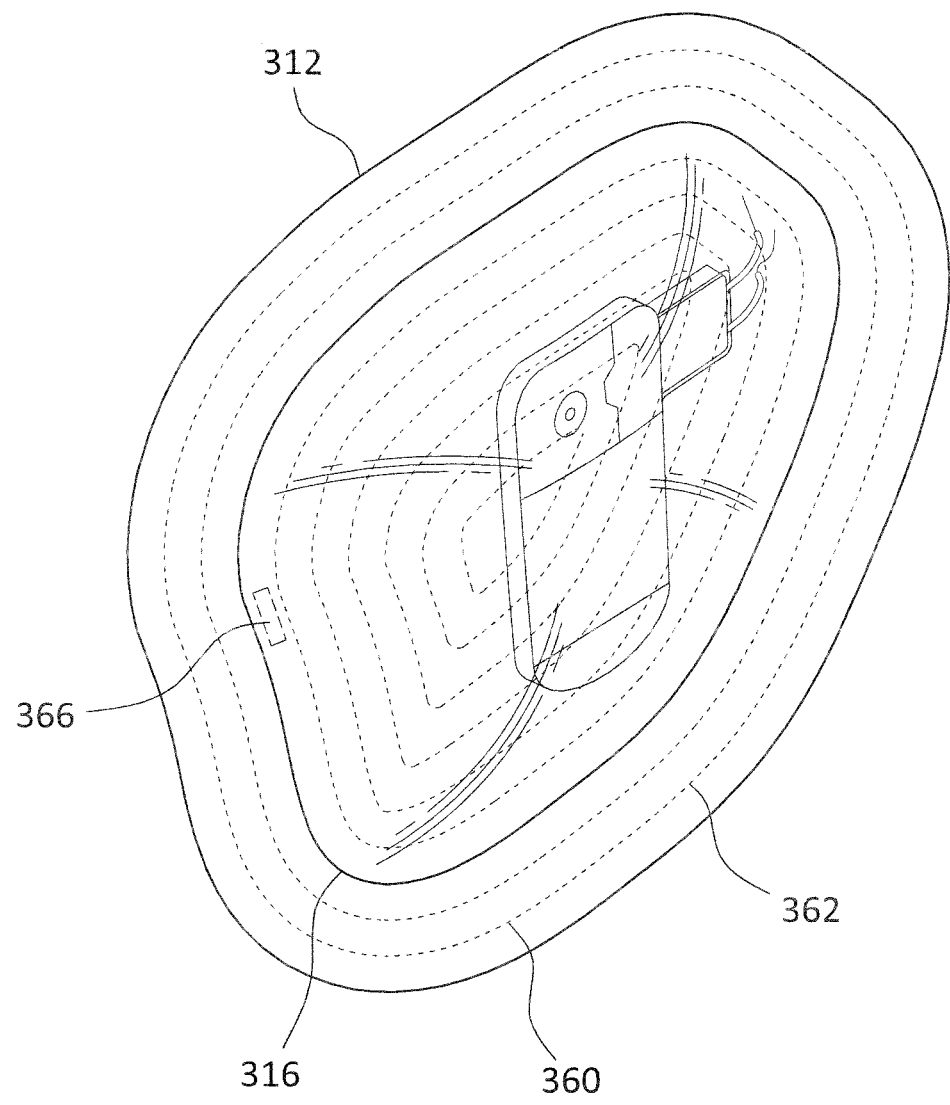
FIGS. 24A and 24B are perspective views of the universal low-profile intercranial assembly in accordance with alternate embodiments of the present invention.
Figure 24B:
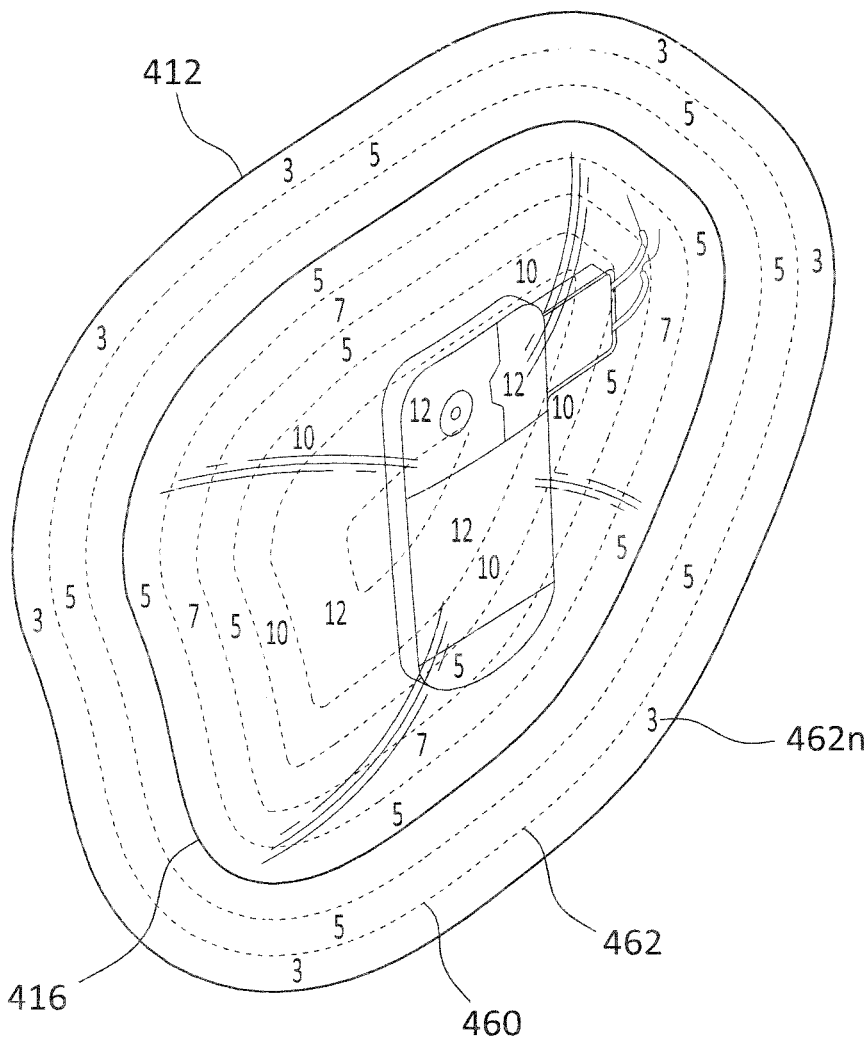

In particular, and as shown in FIGS. 24A to 24B, the mounting plate 312, 412 and the static cranial implant 316, 416 are provided with topographical markings 360, 460. In accordance with a preferred embodiment of the present invention, the topographical markings 360, 460 are composed of contour lines 362, 462 produced by connecting points of the static cranial implant 316, 416 or mounting plate 312, 412 having equal thickness together to create a continuous line. As a specific contour line designates a specific thickness of the mounting plate 312, 412 and the static cranial implant 316, 416, the thickness designated by specific the contour lines is established in a systematic manner. For example, contour lines 362 of a specific color could designate a specific thickness or contour lines 462 could be annotated with numbers 262$n$ indicating the thickness in much the same manner contour lines are used in topographic maps. Where the contour lines 362 are designated by colors, the mounting plate and/or the cranial implant may be provided with a key 366 specifying the meaning of the various colors. It is further appreciated the contour lines may be formed via various known mechanisms, for example, laser etching, molding, 3-D printing, etc.

The contour lines themselves may be formed on the outer first surface(s) of the mounting plate 312, 412 and/or the static cranial implant 316, 416, the inner second surface(s) of the mounting plate 312, 412 and/or the static cranial implant 316, 416, or within the mounting plate 312, 412 and/or the static cranial implant 316, 416 at a position between the outer first surface(s) and inner second surface(s).

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A cranial assembly, comprising:
   a cranial implant including an outer first surface, an inner second surface, and a peripheral edge extending between the outer first surface and the inner second surface, the cranial implant including topographical markings indicating thickness of the cranial implant and allowing a surgeon to readily and accurately appreciate the thickness of the cranial implant, the topographical markings are composed of contour lines produced by connecting points of equal thickness together to create a continuous line designating a specific thickness of the cranial implant at the contour line.

2. The cranial assembly according claim 1, further including an interdigitating functional neurosurgical implant housed within the cranial implant.

3. The cranial assembly according claim 1, further including a mounting plate shaped and dimensioned mounting of the cranial implant therein, the mounting plate including an outer first surface, an inner second surface, and a peripheral edge extending between the outer first surface and the inner second surface.

4. The cranial assembly according claim 3, wherein the mounting plate is made of a clear material and is fully lucent and transparent.

5. The cranial assembly according claim 1, wherein the cranial implant is made of a clear material and is fully lucent and transparent.

6. The cranial assembly according claim 5, wherein the clear material is (Poly(methyl methacrylate)).

7. The cranial assembly according claim 1, wherein the contour lines are composed of specific colors designating a specific thickness.

8. The cranial assembly according claim 1, wherein the contour lines are annotated with numbers indicating the thickness of the cranial implant.

* * * * *